United States Patent [19]

Morisawa et al.

[11] Patent Number: 5,378,689
[45] Date of Patent: Jan. 3, 1995

[54] PEPTIDES HAVING RENIN INHIBITORY ACTIVITY, THEIR PREPARATION AND USE

[75] Inventors: Yasuhiro Morisawa; Mitsuru Kataoka; Yuichiro Yabe; Hiroyuki Koike; Hidekuni Takahagi; Yasuteru Iijima, all of Hiromachi; Tatsuo Kokubu, Osakasayama; Kunio Hiwada, Ehime, all of Japan

[73] Assignee: Sankyo Company, Limited, Tokyo, Japan

[21] Appl. No.: 98,746

[22] Filed: Jul. 28, 1993

Related U.S. Application Data

[63] Continuation of Ser. No. 979,442, Nov. 20, 1992, abandoned, which is a continuation of Ser. No. 480,060, Feb. 14, 1990, abandoned.

[30] Foreign Application Priority Data

Feb. 16, 1989 [JP] Japan .................................. 1-37097
Jun. 14, 1989 [JP] Japan .................................. 1-149577

[51] Int. Cl.$^6$ ..................... A61K 37/02; C07K 5/08
[52] U.S. Cl. ........................................ 514/18; 514/19; 530/331
[58] Field of Search ................. 514/18, 19; 530/331

[56] References Cited

U.S. PATENT DOCUMENTS

| | | | |
|---|---|---|---|
| 4,548,926 | 10/1985 | Matsueda et al. | 514/19 |
| 4,698,329 | 10/1987 | Matsueda et al. | 514/19 |
| 4,727,060 | 2/1988 | Bühlmayer et al. | 514/19 |
| 4,758,584 | 7/1988 | Bühlmayer et al. | 514/19 |
| 4,839,357 | 6/1989 | Patchett et al. | 514/235.8 |

FOREIGN PATENT DOCUMENTS

| | | |
|---|---|---|
| 0173431 | 3/1986 | European Pat. Off. . |
| 0186977 | 7/1986 | European Pat. Off. . |
| 0228192 | 7/1987 | European Pat. Off. . |
| 0274259 | 7/1988 | European Pat. Off. . |
| 0278158 | 8/1988 | European Pat. Off. . |
| 0297816 | 1/1989 | European Pat. Off. . |
| 0326364 | 8/1989 | European Pat. Off. . |
| 58-39149 | 8/1983 | Japan . |
| 61-275256 | 12/1986 | Japan . |
| 87/04349 | 7/1987 | WIPO . |

*Primary Examiner*—Lester L. Lee
*Attorney, Agent, or Firm*—Frishauf, Holtz, Goodman & Woodward

[57] ABSTRACT

Compounds of formula (I):

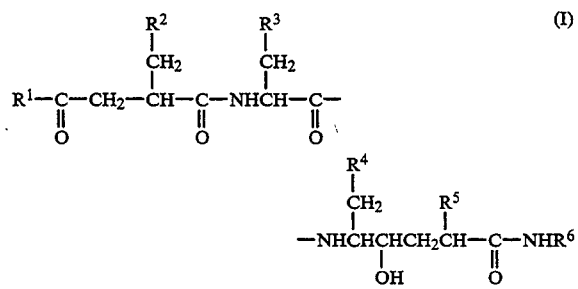

[in which: $R^1$ is heterocyclic group having 5 or 6 ring atoms, or $-NR^7R^8$, where $R^7$ is alkyl and $R^8$ is optionally substituted phenyl, optionally substituted phenylalkyl or cycloalkyl; $R^2$ is optionally substituted phenyl or naphthyl; $R^3$ is thiazolyl; $R^4$ is cyclohexyl or isopropyl; $R^5$ is alkyl; and $R^6$ is alkyl] and salts thereof have renin-inhibitory and, hence, hypotensive activities and are of value in the diagnosis and treatment of hypertension induced by failures in the renin-angiotensin system. They may be prepared by reacting together appropriate amino acids or derivatives thereof.

52 Claims, No Drawings

PEPTIDES HAVING RENIN INHIBITORY ACTIVITY, THEIR PREPARATION AND USE

This application is a continuation of application Ser. No. 07/979,442, filed Nov. 20, 1992 and now abandoned which is a continuation of application Ser. No. 07/480,060 filed Feb. 14, 1990 (abandoned).

BACKGROUND OF THE INVENTION

The present invention relates to a series of new oligopeptides which have renin-inhibitory and, hence, hypotensive activities and thus are of particular value in the diagnosis and treatment of hypertension induced by failures in the renin-angiotensin system. The invention also relates to the preparation of such compounds and to their use in such treatment.

There is considerable evidence that reduction of elevated blood pressure reduces the risks of morbidity and mortality. Elevated blood pressure (hypertension) can be caused by a variety of factors and a large number of drugs is available for the treatment of hypertension, the drug of choice being dictated in large measure by the cause of the hypertension.

Angiotensin I is a polypeptide formed in vivo by the action of renin upon a plasma protein; it is converted in vivo to angiotensin II by the action of ACE (angiotensin converting enzyme). Angiotensin II causes constriction of the arterioles and can produce hypertension. Hypertension of this type can be reduced by reducing the plasma concentration of angiotensin II which, in turn, can be achieved by inhibiting the activity of renin. The number of available drugs having this type of inhibitory activity is very limited, and, to date, no such drug is commercially available. A variety of peptide derivatives having this type of activity is known.

Examples of known peptide derivatives possessing renin inhibitory activity include, for example, the tetrapeptide, tripeptide and like derivatives as described, for example, in Japanese Patent Publication No. Sho 58-39149, in Japanese Patent Kokai Publication No. Sho 61-275256, in European Patent Publications No. 152 255, 173 481, 184 550, 236 734, 278 158 and 297 816, and in WIPO Publication No. 87/04 349. Those prior art compounds believed to be closest to the compounds of the present invention, are disclosed in European Patent Publications No. 184 550, 236 734 and 278 158.

A serious disadvantage common to almost all of the known renin-inhibitory oligopeptides, including many of those mentioned in the previous paragraph, is that, in practice, it is necessary to administer them by parenteral routes, e.g. by injection, as suppositories or even by inhalation. This applies even in those cases where the compounds have been suggested for oral use, since it has often subsequently been found that they either are insufficiently stable to enzymes, e.g. esterases, present in the digestive system or are inadequately absorbed from the stomach and/or intestines or both. Of course, this poor stability in the digestive system is expected with oligopeptides, as the mammalian digestive system is specifically designed to break down compounds of that type. Consequently, even if the compounds can be administered orally, such high doses are necessary in order to make up for poor absorption and/or losses caused by digestion as to make oral administration impractical.

It is, of course, well known that the oral route is the preferred route of administration, particularly where (as with the drugs with which the present invention is concerned)drugs are intended for self-administration by the patient, generally over a long period of time.

Hence, the inability of many of the known renin-inhibitory oligopeptides to be effective when administered via the oral route is a serious disadvantage to their practical therapeutic use, despite what may appear to be their useful activities.

We have now discovered a series of peptide derivatives having a very marked ability to inhibit the activity of renin, which ability is believed to be significantly better than that of the prior art compounds. However, most significantly and surprisingly, the compounds of the invention have been found to have excellent absorptive properties (especially through the intestinal and digestive tracts) upon oral administration, quite contrary to what has been generally experienced with most of the prior art oligopeptide compounds. Moreover, certain of the compounds of the invention have additionally and unexpectedly demonstrated very good stability on oral administration (i.e. they are stable to digestive enzymes, e.g. esterases).

These unexpected properties render the compounds of the invention especially suited to oral administration, as well, of course, as to the more traditional parenteral routes of administration.

BRIEF SUMMARY OF INVENTION

The compounds of the invention are peptides, which may be represented by the general formula (I):

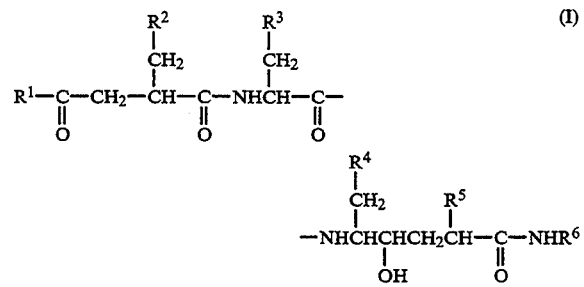

in which:

$R^1$ represents a heterocyclic group having 5 or 6 ring atoms, of which from 1 to 3 are hetero-atoms selected from the group consisting of nitrogen, oxygen and sulfur atoms, said heterocyclic group being unsubstituted or having at least one substituent selected from the group consisting of substituents (a), defined below, or a group of formula

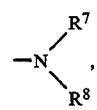

wherein $R^7$ represents a $C_1$-$C_4$ alkyl group and $R^8$ represents an unsubstituted phenyl group, a substituted phenyl group having at least one substituent selected from the group consisting of substituents (b), defined below, a $C_1$-$C_4$ alkyl group having at least one phenyl substituent in which the phenyl substituent is unsubstituted or has at least one substituent selected from the group consisting of substituents (b), defined below, or a $C_5$-$C_8$ cycloalkyl group;

$R^2$ represents an unsubstituted phenyl group, a substituted phenyl group having at least one substituent selected from the group consisting of substituents (b), defined below, an unsubstituted naphthyl group or a substituted naphthyl group having at least one substituent selected from the group consisting of substituents (b), defined below;

$R^3$ represents a thiazolyl group;

$R^4$ represents a cyclohexyl group or an isopropyl group;

$R^5$ represents a $C_1$–$C_4$ alkyl group; and $R^6$ represents a $C_1$–$C_6$ alkyl group;

substituents (a)

$C_1$–$C_4$ alkyl groups, $C_1$–$C_4$ alkoxy groups, halogen atoms, oxygen atoms (i.e. to form an oxo group), unsubstituted phenyl groups and substituted phenyl groups having at least one substituent selected from the group consisting of substituents (b), defined below;

substituents (b)

$C_1$–$C_4$ alkyl groups, $C_1$–$C_4$ alkoxy groups, trifluoromethyl groups and halogen atoms;

and pharmaceutically acceptable salts thereof.

The invention also provides a method for the treatment or prophylaxis of angiotensin-induced hypertension in an animal, especially a mammal, which may be human or non-human, by the administration thereto of an effective amount of a compound of formula (I) or of a pharmaceutically acceptable salt thereof.

The invention still further provides a composition for the treatment or prophylaxis of angiotensin-induced hypertension in an animal, especially a mammal, which may be human or non-human, which comprises an effective amount of a compound of formula (I) or of a pharmaceutically acceptable salt thereof in admixture with a pharmaceutically acceptable carrier or diluent.

The compounds of the invention may be prepared by reacting together two compounds, one having a terminal carboxy group or a reactive derivative thereof and the other having a terminal amino group or a reactive derivative thereof, under conditions conventional for peptide synthesis, said two compounds corresponding to the fragments derivable by cleavage of any one of the peptide bonds in said compound of formula (I). Preferred methods of preparing the compounds are described in greater detail hereafter.

DETAILED DESCRIPTION OF INVENTION

In the compounds of the present invention, where $R^1$ represents a 5- or 6-membered heterocyclic group, it may be a saturated or unsaturated heterocyclic group and if it is an unsaturated heterocyclic group it may be an aromatic or non-aromatic group. However, it is preferably a non-aromatic heterocyclic group, and more preferably a saturated heterocyclic group. It contains from 1 to 3, more preferably 1 or 2 hetero-atoms selected from the group consisting of nitrogen, oxygen and sulfur atoms. Preferably, at least one of the heteroatoms is a nitrogen atom and more preferably the group is attached to the rest of the molecule through that nitrogen atom. Still more preferably it contains at least one nitrogen atom through which it is attached to the remainder of the molecule and 0, 1 or 2, preferably 0 or 1, other hetero-atoms selected from the group consisting of nitrogen, oxygen and sulfur atoms. Examples of such groups include the pyrrolidinyl (e.g. 1-pyrrolidinyl), piperidyl (e.g. 1-piperidyl, i.e. piperidino), morpholinyl (e.g. morpholino), thiomorpholinyl (e.g. thiomorpholino) and piperazinyl (e.g. 1-piperazinyl) groups. Alternative, but less preferred, heterocyclic groups include the thienyl, furyl, pyranyl, pyrrolyl, imidazolyl, pyrazolyl, thiazolyl, isothiazolyl, thiadiazolyl, triazolyl, oxazolyl, isoxazolyl, pyridyl, pyrazinyl, pyrimidinyl, pyridazinyl, furazanyl, pyrrolidinyl, pyrrolinyl, imidazolidinyl, imidazolinyl, pyrazolidinyl, pyrazolinyl and piperazinyl groups. Such groups may be unsubstituted or they may have at least one substituent selected from the group consisting of substituents (a), defined above and exemplified below. Where there is a nitrogen atom other than that (if applicable) through which the group is attached to the rest of the molecule, and where the group is substituted, then we prefer that it should be this nitrogen atom which is substituted. Examples of the groups and atoms which may be included in substituents (a) are:

$C_1$–$C_4$ alkyl groups, which may be straight or branched chain groups, such as the methyl, ethyl, propyl, isopropyl, butyl, sec-butyl, isobutyl and t-butyl groups;

$C_1$–$C_4$ alkoxy groups, which may be straight or branched chain groups, such as the methoxy, ethoxy, propoxy, isopropoxy, butoxy, sec-butoxy, isobutoxy and t-butoxy groups, in which case, these may only be substituents on carbon atoms;

halogen atoms, such as the fluorine, chlorine, bromine and iodine atoms, in which case, these may only be substituents on carbon atoms;

oxygen atoms (i.e. to form an oxo group), in which case, this may only be a substituent on a carbon atom; and unsubstituted phenyl groups and substituted phenyl groups having at least one substituent selected from the group consisting of substituents (b), defined below, for example the phenyl, o-, m- or p- methoxyphenyl, o-, m- or p- ethoxyphenyl, o-, m- or p- chlorophenyl, o-, m- or p- bromophenyl, o-, m- or p- fluorophenyl, o-, m- or p- methylphenyl, o-, m- or p- ethylphenyl and o-, m- or p- trifluoromethylphenyl groups.

Of the groups and atoms listed above as substituents (a), the $C_1$–$C_4$ alkyl, unsubstituted phenyl and substituted phenyl groups are preferred.

Alternatively, $R^1$ may represent a group of formula

wherein $R^7$ and $R^8$ are as defined above.

Where $R^7$ represents a $C_1$–$C_4$ alkyl group, this may be a straight or branched chain group, and examples include the methyl, ethyl, propyl, isopropyl, butyl, sec-butyl, isobutyl and t-butyl groups, of which the methyl, ethyl, propyl, isopropyl, butyl and isobutyl groups are preferred, the methyl group being more preferred.

Alternatively, $R^8$ may represent a $C_1$–$C_4$ alkyl group having at least one phenyl substituent, where the phenyl substituent may itself be substituted or unsubstituted. Where the phenyl substituent is substituted, the substituents are selected from the group consisting of substituents (b), defined above, namely $C_1$–$C_4$ alkyl groups, $C_1$–$C_4$ alkoxy groups, trifluoromethyl groups and halogen atoms. Examples of the alkyl and alkoxy groups and the halogen atoms are as given in relation to the corresponding groups and atoms exemplified in relation to substituents (a), above. Of the alkyl groups which may be substituted by the optionally substituted phenyl group, examples include the methyl, ethyl, propyl, isopropyl, butyl, isobutyl and sec-butyl groups, of which the $C_1$–$C_3$ alkyl groups are preferred, and the methyl and ethyl groups are more preferred, the methyl group being most preferred. Examples of unsubstituted phenylalkyl groups include the benzyl, 1-phenylethyl, phenethyl (2-phenylethyl), 3-phenylpropyl, 2-phenylpropyl and 4-phenylbutyl groups. Examples of substituted phenylalkyl groups include the o-, m- and p- chlorophenyl, o-, m- and p- fluorophenyl, o-, m- and p- bromophenyl, o-, m- and p- methylphenyl, o-, m- and p- methoxyphenyl and o-, m- and p- trifluoromethylphenyl groups. Of the phenylalkyl groups, the preferred groups are the benzyl, phenethyl, 4-methylbenzyl, 4-methoxybenzyl and 4-chlorobenzyl groups.

Alternatively, $R^8$ may represent a phenyl group which may be substituted or unsubstituted. Where it is substituted, the substituents are selected from the group consisting of substituents (b), defined above. Examples of groups and atoms which may be represented by substituents (b) include the alkyl groups, alkoxy groups and halogen atoms exemplified above in relation to the same groups and atoms which may be represented by substituents (a) and the trifluoromethyl group. Of these, the preferred groups are the phenyl, 4-methylphenyl, 4-methoxyphenyl and 4-chlorophenyl groups.

Still further, $R^8$ may represent a $C_5$ or $C_6$ cycloalkyl group, i.e. a cyclopentyl or cyclohexyl group, the cyclohexyl group being preferred.

Where $R^2$ represents a phenyl or naphthyl group, these may be substituted or unsubstituted, and, if substituted, the substituents are selected from the group consisting of substituents (b), defined and exemplifed above. Examples of such groups include the phenyl, o-, m- or p- chlorophenyl, o-, m- or p- fluorophenyl, o-, m- or p- bromophenyl, o-, m- or p- methylphenyl, o-, m- or p- methoxyphenyl, o-, m- or p- trifluoromethylphenyl, 1-naphthyl, 2-naphthyl, 4-chloro-1-naphthyl, 6-chloro-1-naphthyl, 4-fluoro-1-naphthyl, 6-fluoro-1-naphthyl, 4-bromo-1-naphthyl, 6-bromo-1-naphthyl, 4-methyl-1-naphthyl, 6-methyl-1-naphthyl, 4-methoxy-1-naphthyl, 6-methoxy-1-naphthyl, 4-trifluoromethyl-1-naphthyl, 6-trifluoromethyl-1-naphthyl, 4-chloro-2-naphthyl, 6-chloro-2-naphthyl, 4-methyl-2-naphthyl, 6-methyl-2-naphthyl, 4-methoxy-2-naphthyl and 6-methoxy-2-naphthyl groups, of which the phenyl, o-, m- or p- tolyl, o-, m- or p- chlorophenyl, o-, m- or p- methoxyphenyl and 1- and 2- naphthyl groups are preferred.

Where $R^5$ represents a $C_1$–$C_4$ alkyl group, this may be a straight or branched chain group, and examples include the methyl, ethyl, propyl, isopropyl, butyl, sec-butyl, isobutyl and t-butyl groups, of which the methyl, ethyl, propyl, isopropyl and isobutyl groups are preferred.

Where $R^6$ represents a $C_1$–$C_6$ alkyl group, this may be a straight or branched chain group, and examples include the methyl, ethyl, propyl, isopropyl, butyl, isobutyl, sec-butyl, t-butyl, pentyl, isopentyl, hexyl and isohexyl groups, of which the methyl, ethyl, propyl, isopropyl, butyl, isobutyl and hexyl groups are preferred, and the methyl, ethyl, propyl, butyl and isobutyl groups are most preferred.

Examples of preferred groups that may be represented by $R^1$ in the compounds of the present invention include the 1-pyrrolidinyl, piperidino, 2-methylpiperidino, 3-methylpiperidino, 4-methylpiperidino, 2-ethylpiperidino, morpholino, 2,6-dimethylmorpholino, perhydro-1,4-thiazin-4-yl (more commonly known as thiomorpholino), 1-piperazinyl, 4-methyl-1-piperazinyl, 4-phenyl-1-piperazinyl, 4-(p-fluorophenyl)-1-piperazinyl, 4-(p-chlorophenyl)-1-piperazinyl, 4-(o-chlorophenyl)-1-piperazinyl, 4-(m-chlorophenyl)-1-piperazinyl, 4-(o-methoxyphenyl)-1-piperazinyl, 4-(m-trifluoromethylphenyl)-1-piperazinyl, N-phenyl-N-methylamino, N-benzyl-N-methylamino, N-benzyl-N-ethylamino, N-phenethyl-N-methylamino, N-(o-methoxybenzyl)-N-methylamino, N-(p-methoxybenzyl)-N-methylamino, N-(m-methoxybenzyl)-N-methylamino, n-(o-methylbenzyl)-N-methylamino, N-(p-methylbenzyl)-N-methylamino, N-(m-methylbenzyl)-N-methylamino, N-(O-chlorobenzyl)-N-methylamino, N-(p-chlorobenzyl)-N-methylamino, N-(m-chlorobenzyl)-N-methylamino, N-benzyl-N-isopropylamino, N-methyl-N-(p-tolyl)amino and N-cyclohexyl-N-methylamino groups.

Examples of more preferred groups that may be represented by $R^1$ include the 1-pyrrolidinyl, piperidino, morpholino, perhydro-1,4-thiazin-4-yl, 1-piperazinyl, 4-methyl-1-piperazinyl, 4-phenyl-1-piperazinyl, N-benzyl-N-methylamino, N-benzyl-N-ethylamino, N-phenethyl-N-methylamino, N-(o-methoxybenzyl)-N-methylamino, N-(p-methoxybenzyl)-N-methylamino, N-(m-methoxybenzyl)-N-methylamino, N-(o-methylbenzyl)-N-methylamino, N-(p-methylbenzyl)-N-methylamino, N-(m-methylbenzyl)-N-methylamino, N-(o-chlorobenzyl)-N-methylamino, N-(p-chlorobenzyl)-N-methylamino, N-(m-chlorobenzyl)-N-methylamino and N-cyclohexyl-N-methylamino groups.

Examples of preferred groups which may be represented by $R^2$ include the phenyl, o-, m- or p- tolyl, o-, m- or p- chlorophenyl, o-, m- or p- methoxyphenyl, and 1- or 2- naphthyl groups.

An example of a preferred group which may be represented by $R^3$ is the 4-thiazolyl group.

An example of a preferred group which may be represented by $R^4$ is the cyclohexyl group.

Examples of preferred groups which may be represented by $R^5$ include the methyl, ethyl, propyl, isopropyl and isobutyl groups.

Examples of preferred groups which may be represented by $R^6$ include the methyl, ethyl, propyl, isopropyl, butyl, isobutyl and hexyl groups.

Still more preferred groups which may be represented by $R^1$ include the morpholino and N-benzyl-N-methylamino groups, the morpholino group being most preferred.

Still more preferred groups which may be represented by $R^2$ include the phenyl, and the o-, m- and p-methoxyphenyl groups.

Still more preferred groups which may be represented by $R^5$ include the methyl, ethyl and isopropyl groups.

Still more preferred groups which may be represented by $R^6$ include the methyl, ethyl, propyl, butyl and isobutyl groups.

The compounds of the present invention necessarily contain several asymmetric carbon atoms in their molecules, and can thus form optical isomers. Although these are, in general, all represented herein by a single molecular formula, the present invention includes both the individual, isolated isomers and mixtures, including racemates, thereof. Where stereospecific synthesis techniques are employed, individual isomers may be prepared directly; on the other hand, if a mixture of isomers is prepared, the individual isomers may be obtained by conventional resolution techniques. Alternatively, the compounds of the present invention may, if desired, be employed as a mixture of two or more such isomers.

Of the various isomers of the compounds of the present invention, we especially prefer:

those in which the carbon atom indicated by an asterisk in the moiety of formula:

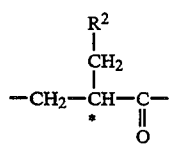

is in the R configuration;

those in which the carbon atom indicated by an asterisk in the moiety of formula:

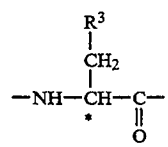

is in the S configuration;

those in which the carbon atom indicated by an asterisk in the moiety of formula:

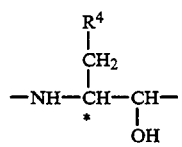

is in the S configuration;

those in which the carbon atom indicated by an asterisk in the moiety of formula:

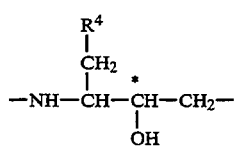

is in the S configuration; and those in which the carbon atom indicated by a double asterisk in the moiety of formula:

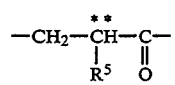

has the configuration:

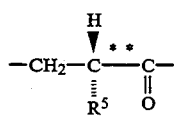

More preferred isomers are those in which:

the carbon atoms indicated by a single asterisk in the moiety of formula:

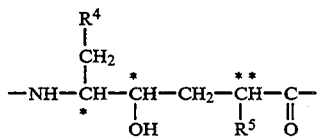

are all in the S configuration and the carbon atom indicated by the double asterisk has the configuration:

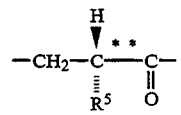

Still more preferably, the carbon atom indicated by an asterisk in the moiety of formula:

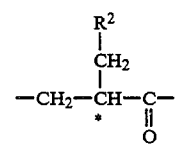

is in the R configuration and all of the carbon atoms indicated by single asterisks in the moiety of formula:

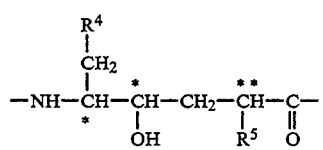

are in the S configuration and the carbon atom indicated by the double asterisk has the configuration:

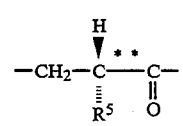

Most preferably, the carbon atom indicated by an asterisk in the moiety of formula:

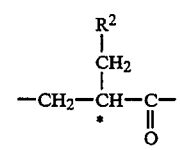

in the R configuration and all of the carbon atoms indicated by single asterisks in the moiety of formula:

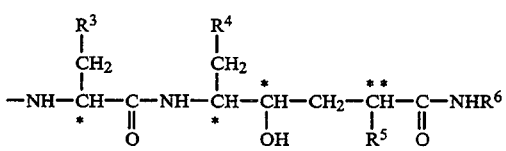

are in the S configuration and the carbon atom indicated by the double asterisk has the configuration:

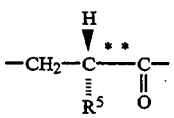

The compounds of the present invention can form salts. There is no particular restriction on the nature of these salts, provided that, where they are intended for therapeutic use, they are pharmaceutically acceptable. Where they are intended for non-therapeutic uses, e.g. as intermediates in the preparation of other, and possibly more active, compounds, even this restriction does not apply. The compounds include several basic nitrogen atoms and can, therefore, form acid addition salts. Examples of such acid addition salts include: salts with a mineral acid, such as hydrochloric acid, sulfuric acid or phosphoric acid; salts with an organic carboxylic acid, such as oxalic acid, maleic acid, succinic acid, tartaric acid, malic acid, malonic acid, acetic acid, fumaric acid, formic acid, benzoic acid, mandelic acid, ascorbic acid, lactic acid, gluconic acid or citric acid; and salts with a sulfonic acid, such as methanesulfonic acid, benzenesulfonic acid, ethanesulfonic acid or p-toluenesulfonic acid.

Also, the compounds may contain a free carboxylic acid group, and, in such a case, can form salts with cations, examples of which include:

metal atoms, especially alkali metal atoms, such as the sodium and potassium atoms, alkaline earth metal atoms, such as the calcium atom, and other atoms, such as the magnesium and aluminum atoms;

the ammonium group;

cations derived from a trialkylamine, such as triethylamine, or from another organic base, such as dicyclohexylamine, procaine, dibenzylamine, phenethylamine, 2-phenylethylbenzylamine, ethanolamine, diethanolamine, a polyhydroxyalkylamine or N-methylglucosamine; and basic amino acids, such as lysine, arginine, ornithine or histidine.

Of the above, we prefer salts of a mineral acid, especially hydrochloric acid, an organic carboxylic acid, especially acetic acid, or a sulfonic acid, especially methanesulfonic acid.

Preferred compounds of the present invention are those of formula (I) in which:

(1) $R^1$ represents a pyrrolidinyl, piperidinyl, morpholinyl, thiomorpholinyl, piperazinyl, 4-methylpiperazinyl or 4-phenylpiperazinyl group or a group of formula

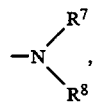

wherein $R^7$ represents a $C_1$-$C_4$ alkyl group and $R^8$ represents a $C_1$-$C_4$ alkyl group having a phenyl substituent, the phenyl substituent being unsubstituted or having at least one substituent selected from the group consisting of methyl groups, ethyl groups, methoxy groups and chlorine atoms;

(2) $R^2$ represents a phenyl, tolyl, chlorophenyl, methoxyphenyl or naphthyl group;

(3) $R^6$ represents a methyl, ethyl, propyl, isopropyl, butyl, isobutyl or hexyl group.

In particular, preferred compounds are those in which $R^1$ is as defined in (1) above, $R^2$ is as defined in (2) above and $R^6$ is as defined in (3) above.

More preferred compounds are those compounds of formula (I) in which:

(4) $R^1$ represents a pyrrolidinyl, piperidinyl, morpholinyl, thiomorpholinyl, piperazinyl, 4-methylpiperazinyl or 4-phenylpiperazinyl group or a group of formula

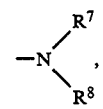

wherein $R^7$ represents a methyl or ethyl group and $R^8$ represents a benzyl, phenethyl, 4-methylbenzyl, 4-methoxybenzyl or 4-chlorobenzyl group.

In particular, more preferred compounds are those in which $R^1$ is as defined in (4) above, $R^2$ is as defined in (2) above and $R^6$ is as defined in (3) above.

Still more preferred compounds are those compounds of formula (I) in which:

(5) $R^1$ represents a morpholinyl or N-benzyl-N-methylamino group;

(6) $R^2$ represents a phenyl or methoxyphenyl group;

(7) $R^4$ represents a cyclohexyl group;

(8) $R^5$ represents a methyl, ethyl or isopropyl group;

(9) $R^6$ represents a methyl, ethyl, propyl, butyl or isobutyl group.

In particular, still more preferred compounds are those in which $R^1$ is as defined in (5) above $R^2$ is as defined in (6) above, $R^4$ is as defined in (7) above, $R^5$ is as defined in (8) above and $R^6$ is as defined in (9) above.

Most preferred of the heterocyclic groups represented by $R^1$ are those attached to the remainder of the molecule via their nitrogen atoms, i.e. those in classes (1), (4) and (5).

Also preferred are the salts of the above preferred and more preferred compounds, especially the hydrochlorides, acetates and methanesulfonates.

Specific examples of compounds of the present invention are listed in the following Table 1, in which the compounds have the formula (I), shown above, and $R^1$, $R^2$, $R^4$, $R^5$ and $R^6$ are as shown in the Table. In the Table, the following abbreviations are used and have the meanings defined below:

| | |
|---|---|
| Bu | butyl |
| iBu | isobutyl |
| Bz | benzyl |
| Et | ethyl |
| Hx | hexyl |
| cHx | cyclohexyl |
| Me | methyl |
| Mor | morpholino |
| Np | naphthyl |
| Ph | phenyl |
| Pip | 1-piperidyl |
| Pr | propyl |
| iPr | isopropyl |
| Piz | 1-piperazinyl |
| Pyrd | 1-pyrrolidinyl |
| Thz | perhydro-1,4-thiazin-4-yl (=thiomorpholino) |

TABLE 1

| Cpd No. | R¹ | R² | R⁴ | R⁵ | R⁶ |
|---|---|---|---|---|---|
| 1 | Mor | Ph | cHx | Me | Me |
| 2 | Mor | Ph | cHx | Me | Et |
| 3 | Mor | Ph | cHx | Me | iPr |
| 4 | Mor | Ph | cHx | Me | Bu |
| 5 | Mor | Ph | cHx | Me | Hx |
| 6 | Mor | Ph | cHx | Et | Me |
| 7 | Mor | Ph | cHx | iPr | Me |
| 8 | Mor | Ph | cHx | iPr | Bu |
| 9 | Mor | Ph | cHx | iPr | Hx |
| 10 | Mor | Ph | iPr | Me | Me |
| 11 | Mor | Ph | iPr | iPr | Bu |
| 12 | Mor | 4-MeOPh | cHx | Me | Me |
| 13 | Mor | 4-MeOPh | cHx | Me | Et |
| 14 | Mor | 4-MeOPh | cHx | Me | iPr |
| 15 | Mor | 4-MeOPh | cHx | Me | Bu |
| 16 | Mor | 4-MeOPh | cHx | Et | Me |
| 17 | Mor | 4-MeOPh | cHx | iPr | Me |
| 18 | Mor | 4-MeOPh | cHx | iPr | Et |
| 19 | Mor | 4-MeOPh | cHx | iPr | Bu |
| 20 | Mor | 4-MeOPh | iPr | Me | Me |
| 21 | Mor | 3-MeOPh | cHx | Me | Me |
| 22 | Mor | 2-MeOPh | cHx | iPr | Me |
| 23 | Mor | 4-MePh | cHx | iPr | Bu |
| 24 | Mor | 1-Np | cHx | Me | Me |
| 25 | Mor | 1-Np | cHx | Me | Bu |
| 26 | Mor | 1-Np | cHx | iPr | Me |
| 27 | Mor | 1-Np | cHx | iPr | Et |
| 28 | Mor | 1-Np | cHx | iPr | Bu |
| 29 | Thz | Ph | cHx | Me | Me |
| 30 | Thz | 4-MeOPh | cHx | iPr | Bu |
| 31 | Pip | Ph | cHx | Me | Me |
| 32 | Pyrd | Ph | cHx | Me | Bu |
| 33 | Bz(Me)N— | Ph | cHx | Me | Me |
| 34 | Bz(Me)N— | Ph | cHx | Me | Et |
| 35 | Bz(Me)N— | Ph | cHx | Me | Pr |
| 36 | Bz(Me)N— | Ph | cHx | Me | iPr |
| 37 | Bz(Me)N— | Ph | cHx | Me | Bu |
| 38 | Bz(Me)N— | Ph | cHx | Me | iBu |
| 39 | Bz(Me)N— | Ph | cHx | Me | Hx |
| 40 | Bz(Me)N— | Ph | cHx | Et | Me |
| 41 | Bz(Me)N— | Ph | cHx | iPr | Me |
| 42 | Bz(Me)N— | Ph | cHx | iPr | Et |
| 43 | Bz(Me)N— | Ph | cHx | ipr | Pr |
| 44 | Bz(Me)N— | Ph | cHx | iPr | Bu |
| 45 | Bz(Me)N— | Ph | CHX | iPr | Hx |
| 46 | Bz(Me)N— | Ph | iPr | Me | Me |
| 47 | Bz(Me)N— | Ph | iPr | Me | iPr |
| 48 | Bz(Me)N— | Ph | iPr | Me | Bu |
| 49 | Bz(Me)N— | Ph | iPr | Me | iBu |
| 50 | Bz(Me)N— | Ph | iPr | iPr | Me |
| 51 | Bz(Me)N— | Ph | iPr | iPr | Bu |
| 52 | Bz(Me)N— | 4-MeOPh | cHx | Me | Me |
| 53 | Bz(Me)N— | 4-MeOPh | cHx | Me | iPr |
| 54 | Bz(Me)N— | 4-MeOPh | cHx | Me | Bu |
| 55 | Bz(Me)N— | 4-MeOPh | cHx | Me | iBu |
| 56 | Bz(Me)N— | 4-MeOPh | cHx | iPr | Me |
| 57 | Bz(Me)N— | 4-MeOPh | cHx | iPr | Bu |
| 58 | Bz(Me)N— | 4-MeOPh | iPr | Me | Me |
| 59 | Bz(Me)N— | 4-MeOPh | iPr | Me | Bu |
| 60 | Bz(Me)N— | 2-MeOPh | cHx | Me | Me |
| 61 | Bz(Me)N— | 3-MeOPh | cHx | Me | Bu |
| 62 | Bz(Me)N— | 4-MePh | cHx | Me | Me |
| 63 | Bz(Me)N— | 4-ClPh | cHx | Me | Bu |
| 64 | Bz(Me)N— | 1-Np | cHx | Me | Me |
| 65 | Bz(Me)N— | 1-Np | cHx | iPr | Me |
| 66 | Bz(Et)N— | Ph | cHx | Me | Me |
| 67 | Bz(Et)N— | Ph | cHx | Me | Bu |
| 68 | Bz(Et)N— | Ph | cHx | iPr | Me |
| 69 | Bz(Et)N— | Ph | cHx | iPr | Bu |
| 70 | Bz(Et)N— | 4-MeOPh | cHx | Me | Me |
| 71 | 2-PhEt(Me)N— | Ph | cHx | Me | Me |
| 72 | 2-PhEt(Me)N— | Ph | cHx | Me | Bu |
| 73 | 2-PhEt(Me)N— | Ph | cHx | iPr | Me |
| 74 | Ph(Me)N— | Ph | cHx | Me | Me |
| 75 | cHx(Me)N— | Ph | cHx | Me | Bu |
| 76 | 4-MeBz(Me)N— | Ph | cHx | Me | Me |
| 77 | 4-MeOBz(Me)N— | Ph | c.Hx | Me | Me |
| 78 | 4-ClBz(Me)N— | Ph | cHx | Me | Me |
| 79 | 4-MePiz | 4-MeOPh | cHx | Me | Bu |
| 80 | Pip | 4-MeOPh | cHx | Me | Bu |
| 81 | Mor | Ph | cHx | iPr | Et |
| 82 | Mor | Ph | cHx | iPr | Pr |

Of the compounds listed above, the preferred compounds are Compounds No. 1, 2, 3, 4, 5, 6, 7, 8, 9, 10, 11, 12, 13, 14, 15, 16, 17, 18, 19, 20, 21, 22, 33, 34, 35, 36, 37, 38, 41, 44, 54, 75, 79, 80, 81 and 82, and the more preferred compounds are:

1. 5-{N-[2-Benzyl-3-(morpholinocarbonyl)propionyl]-3-(4-thiazolyl)-L-alanyl}amino-6-cyclohexyl-4-hydroxy-2,N-dimethylhexanamide, especially the (2R, 4R, 5S)-5-{N-[2(R)-benzyl-3-(morpholinocarbonyl)propionyl]-3-(4-thiazolyl)-L-alanyl}amino-6-cyclohexyl-4-hydroxy-2,N-dimethylhexanamide isomer;

4. 5-{N-[2-Benzyl-3-(morpholinocarbonyl)propionyl]-3-(4-thiazolyl)-L-alanyl}amino-N-butyl-6-cyclohexyl-4-hydroxy-2-methylhexanamide, especially the (2R, 4S, 5S)-5-{N-[2(R)-benzyl-3-(morpholinocarbonyl)propionyl]-3-(-4-thiazolyl)-L-alanyl}amino-N-butyl-6-cyclohexyl-4-hydroxy-2-methylhexanamide isomer;

5. 5-{N-[2-Benzyl-3-(morpholinocarbonyl)propionyl]-3-(4-thiazolyl)-L-alanyl}amino-6-cyclohexyl-N-hexyl-4-hydroxy-2-methylhexanamide, especially the (2R, 4S, 5S)-5-{N-[2(R)-benzyl-3-(morpholinocarbonyl)propionyl]-3-(4-thiazolyl)-L-alanyl}amino-6-cyclohexyl-N-hexyl-4-hydroxy-2-methylhexanamide isomer;

7. 5-{N-[2-Benzyl-3-(morpholinocarbonyl)propionyl]-3-(4-thiazolyl)-L-alanyl}amino-6-cyclohexyl-4-hydroxy-2-isopropyl-N-methylhexanamide, especially the (2S, 4S, 5S)-5-{N-[2(R)-benzyl-3-(morpholinocarbonyl)propionyl]-3-(4-thiazolyl)-L-alanyl}amino-6-cyclohexyl-4-hydroxy-2-isopropyl-N-methylhexanamide isomer;

8. 5-{N-[2-Benzyl-3-(morpholinocarbonyl)propionyl]-3-( 4-thiazolyl)-L-alanyl}amino-N-butyl-6-cyclohexyl-4-hydroxy-2-isopropylhexanamide, especially the (2S, 4S, 5S)-5-{N-[2(R)-benzyl-3-(morpholinocarbonyl)propionyl]-3-(4-thiazolyl)-L-alanyl}amino-N-butyl-6-cyclohexyl-4-hydroxy-2-isopropylhexanamide isomer;

15. N-Butyl-6-cyclohexyl-4-hydroxy-5-{N-[2-(4-methoxybenzyl)-3-(morpholinocarbonyl)propionyl]-3-(4-thiazolyl)-L-alanyl}amino-2-methylhexanamide, especially the (2R, 4S, 5S)-N-butyl-6-cyclohexyl-4-hydroxy-5-{N-[2(R)-(4-methoxybenzyl)-3-(morpholinocarbonyl)propionyl]-3-(4-thiazolyl)-L-alanyl}amino-2-methylhexanamide isomer;

17. 5-{N-[2-(4-Methoxybenzyl)-3-(morpholinocarbonyl)propionyl]-3-(4-thiazolyl)-L-alanyl}amino-6-cyclohexyl-4-hydroxy-2-isopropyl-N-methylhexanamide, especially the (2S, 4S, 5S)-5-{N-[2(R)-(4-methoxybenzyl)-3-(morpholinocarbonyl)propionyl]-3-(4-thiazolyl)-L-alanyl}amino-6-cyclohexyl-4-hydroxy-2-isopropyl-N-methylhexanamide isomer;

19. N-Butyl-6-cyclohexyl-4-hydroxy-2-isopropyl-5-{N-[2-(4-methoxybenzyl)-3-(morpholinocarbonyl)propionyl]-3-(4-thiazolyl)-L-alanyl}aminohexanamide, especially the (2S, 4S, 5S)-N-butyl-6-cyclohexyl-4-hydroxy-2-isopropyl-5-{N-[2(R)-(4-methoxybenzyl)-3-(morpholinocarbonyl)propionyl]-3-(4-thiazolyl)-L-alanyl}aminohexanamide isomer;

33. 5-{N-[2-Benzyl-3-(N-benzyl-N-methylaminocarbonyl)propionyl]-3-(4-thiazolyl)-L-alanyl}amino-6-cyclohexyl-4-hydroxy-2,N-dimethylhexanamide, especially the (2R, 4S, 5S)-5-{N-[2(R)-benzyl-3-(N-benzyl-N-methylaminocarbonyl)propionyl]-3-(4-thiazolyl)-L-alanyl}amino-6-cyclohexyl-4-hydroxy-2,N-dimethylhexanamide isomer;

34. 5-{N-[2-Benzyl-3-(N-benzyl-N-methylaminocarbonyl)propionyl]-3-(4-thiazolyl)-L-alanyl}amino-6-cyclohexyl-N-ethyl-4-hydroxy-2-methylhexanamide, especially the (2R, 4S, 5S)-5-{N-[2(R)-benzyl-3-(N-benzyl-N-methylaminocarbonyl)propionyl]-3-(4-thiazolyl)-L-alanyl}amino-6-cyclohexyl-N-ethyl-4-hydroxy-2-methylhexanamide isomer;

35. 5-{N-[2-Benzyl-3-(N-benzyl-N-methylaminocarbonyl)propionyl]-3-(4-thiazolyl)-L-alanyl}amino-6-cyclohexyl-4-hydroxy-2-methyl-N-propylhexanamide, especially the (2R, 4S, 5S)-5-{N-[2(R)-benzyl-3-(N-benzyl-N-methylaminocarbonyl)propionyl]-3-(4-thiazolyl)-L-alanyl}amino-6-cyclohexyl-4-hydroxy-2-methyl-N-propylhexanamide isomer;

36. 5-{N-[2-Benzyl-3-(N-benzyl-N-methylaminocarbonyl)propionyl]-3-(4-thiazolyl)-L-alanyl}amino-6-cyclohexyl-4-hydroxy-N-isopropyl-2-methylhexanamide, especially the (2R, 4S, 5S)-5-{N-[2(R)-benzyl-3-(N-benzyl-N-methylaminocarbonyl)propionyl]-3-(4-thiazolyl)-L-alanyl}amino-6-cyclohexyl-4-hydroxy-N-isopropyl-2-methylhexanamide isomer;

37. 5-{N-[2-Benzyl-3-(N-benzyl-N-methylaminocarbonyl)propionyl]-3-(4-thiazolyl)-L-alanyl}amino-N-butyl-6-cyclohexyl-4-hydroxy-2-methylhexanamide, especially the (2R, 4S, 5S)-5-{N-[2(R)-benzyl-3-(N-benzyl-N-methylaminocarbonyl)propionyl]-3-(4-thiazolyl)-L-alanyl}amino-N-butyl-6-cyclohexyl-4-hydroxy-2-methylhexanamide isomer;

38. 5-{N-[2-Benzyl-3-(N-benzyl-N-methylaminocarbonyl)propionyl]-3-(4-thiazolyl)-L-alanyl}amino-6-cyclohexyl-4-hydroxy-N-isobutyl-2-methylhexanamide, especially the (2R, 4S, 5S)-5-{N-[2(R)-benzyl-3-(N-benzyl-N-methylaminocarbonyl)propionyl]-3-(4-thiazolyl)-L-alanyl}amino-6-cyclohexyl-4-hydroxy-N-isobutyl-2-methylhexanamide isomer;

41. 5-{N-[2-Benzyl-3-(N-benzyl-N-methylaminocarbonyl)propionyl]-3-(4-thiazolyl)-L-alanyl}amino-6-cyclohexyl-4-hydroxy-2-isopropyl-N-methylhexanamide, especially the (2S, 4S, 5S)-5-{N-[2(R)-benzyl-3-(N-benzyl-N-methylaminocarbonyl)propionyl]-3-(4-thiazolyl)-L-alanyl}amino-6-cyclohexyl-4-hydroxy-2-isopropyl-N-methylhexanamide isomer;

44. 5-{N-[2-Benzyl-3-(N-benzyl-N-methylaminocarbonyl)propionyl]-3-(4-thiazolyl)-L-alanyl}amino-N-butyl-6-cyclohexyl-4-hydroxy-2-isopropylhexanamide, especially the (2S, 4S, 5S)-5-{N-[2(R)-benzyl-3-(N-benzyl-L-methylaminocarbonyl)propionyl]-3-(4-thiazolyl)-L-alanyl}amino-N-butyl-6-cyclohexyl-4-hydroxy-2-isopropylhexanamide isomer;

54. N-Butyl-6-cyclohexyl-4-hydroxy-5-{N-[2-(4-methoxybenzyl)-3-(N-benzyl-N-methylaminocarbonyl)propionyl]-3-(4-thiazolyl)-L-alanyl}amino-2-methylhexanamide, especially the (2R, 4S, 5S)-N-butyl-6-cyclohexyl-4-hydroxy-5-{N-[2(R)-(4-methoxybenzyl)-3-(N-benzyl-N-methylaminocarbonyl)propionyl]-3-(4-thiazolyl)-L-alanyl}amino-2-methylhexanamide isomer;

and pharmaceutically acceptable salts thereof, especially the hydrochlorides and the most preferred are Compounds No. 1, 4, 5, 7, 8, 15, 17 and 19 and pharmaceutically acceptable salts thereof, especially the hydrochlorides.

The compounds of the present invention are oligopeptides and may, therefore, be prepared, as is well known in the art, by reacting together the component amino acids or functional derivatives thereof in any appropriate order, by reacting together two or more lower oligopeptides or functional derivatives thereof (again, if necessary, in any appropriate order) or by reacting one or more component amino acids or functional derivatives thereof with one or more lower oligopeptides or functional derivatives thereof (again, if necessary, in any appropriate order). However, provided that the correct sequence of amino acid residues in the oligopeptide of formula (I) is achieved, there is no particular restriction upon the order in which these reactions are carried out. In general terms, the compounds of the invention may be prepared by reacting together compounds of formulae:

$$R^{1'}—H \quad (II) \quad or \quad R^{1''}—X \qquad (IIa)$$

or a reactive derivative thereof,

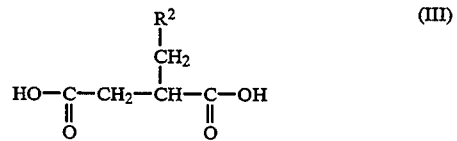

or a reactive derivative thereof,

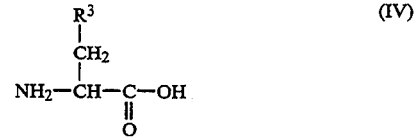

or a reactive derivative thereof,

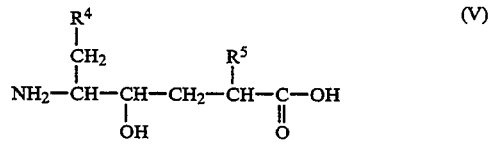

or a reactive derivative thereof,

$$NH_2—R^6 \qquad (VI)$$

or a reactive derivative thereof [in the above formulae $R^2$–$R^6$ are as defined above; $R^{1'}$ represents a heterocyclic group as defined for $R^1$ which is attached to the hydrogen atom shown in the compound of formula (II) via a ring nitrogen atom; $R^{1''}$ represents a heterocyclic group as defined for $R^1$ which is attached to the atom represented by X in formula (IIa) via a ring carbon atom; and X represents a halogen atom];

or by reacting a peptide compound derivable by reaction of some of said compounds of formulae (II), (IIa), (III), (IV), (V) or (VI) or said reactive derivatives with the remainder of said compounds or said reactive derivative(s) or with a peptide compound or compounds derivable by reaction of said remainder or reactive derivative(s) thereof, the reaction(s) being in an order corresponding to the order of the residues derived from said compounds of formulae (II), (IIa), (III), (IV), (V) and (VI) in said compound of formula (I).

If required, the resulting compound of formula (I) may be subjected to any one or more of various optional reactions, for example salification.

In specific embodiments of the process of the present invention, the compounds of the invention may be prepared by any of the following Reaction Schemes A, B and C.

(VIII). This is a standard condensation reaction of the type conventionally used in peptide synthesis and it may be carried out according to any of the well known techniques conventionally employed in peptide synthesis, for example by the azide method, the active ester method, the mixed acid anhydride method or the condensation method. The reactive derivatives employed in these reactions are those reactive derivatives conventionally employed in such methods. Certain of these methods are described in more detail below.

Method A:

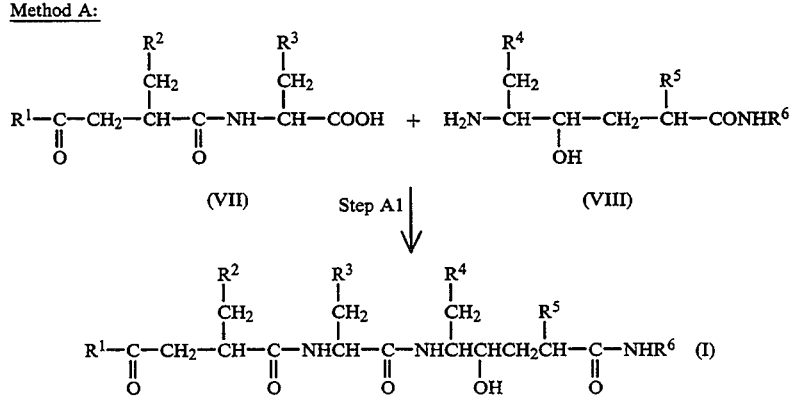

Method B:

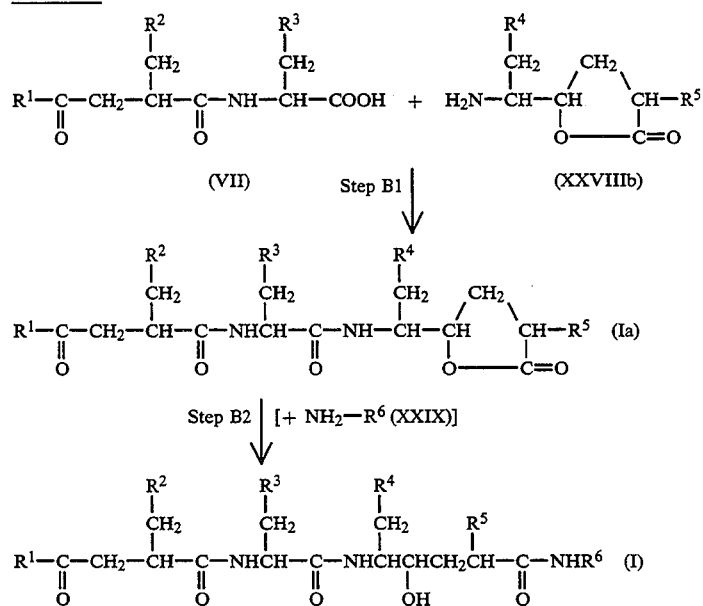

Method C:

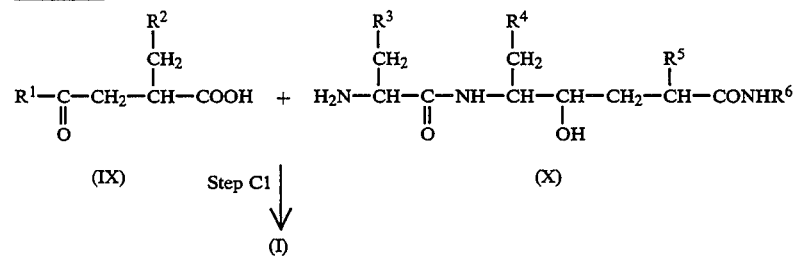

In the above formulae, $R^1$, $R^2$, $R^3$, $R^4$, $R^5$ and $R^6$ are as defined above.

In Method A (Step A1), a compound of formula (I) is prepared by reacting a compound of formula (VII) or a reactive derivative thereof with a compound of formula

Azide Method

First, the carboxylic acid of formula (VII) as such, or, more usually, in the form of its corresponding alkyl ester, is treated with hydrazine in an inert solvent, to give the corresponding acid hydrazide. The nature of the solvent employed in this reaction is not critical and any solvent commonly employed in this type of reaction may equally be employed here, provided that it has no adverse effect on the reaction; however, we generally find it convenient to use a polar solvent, especially a fatty acid amide, such as dimethylformamide. Also, the reaction temperature is not critical and the reaction will take place over a wide range of temperatures; we generally find it convenient to carry out the reaction at a temperature of from 0° C. to about ambient temperature.

The resulting hydrazide is then reacted with a nitrite, to convert it into an azide, after which the azide is reacted with the amine of formula (VIII).

Examples of nitrites which may be employed include: alkali metal nitrites, such as sodium nitrite; and alkyl nitrites, such as isoamyl nitrite.

The reaction of the acid hydrazide with the nitrite and the subsequent reaction of the resulting azide with the amine of formula (VIII) are commonly carried out in the same reaction solution, without intermediate isolation of the azide. Both reactions are preferably carried out in the presence of an inert solvent. The nature of the solvent is not critical, provided that it does not interfere with the reaction. Suitable solvents for these reactions include, for example: amides, especially fatty acid amides, such as dimethylformamide or dimethylacetamide; sulfoxides, such as dimethyl sulfoxide; and pyrrolidones, such as N-methylpyrrolidone. Although there is no criticality as to the reaction temperature, the reaction with the nitrite is preferably effected at a relatively low temperature, e.g. from −50° C. to 0° C., whilst the reaction of the azide with the amine is preferably effected at a temperature of from −10° C. to +10° C. The time required for each of these reactions will vary, depending upon the nature of the reagents and the reaction temperature, but, under the preferred conditions outlined above, a period of from 5 minutes to 1 hour and a period of from 10 hours to 5 days will normally suffice for the reaction with the nitrite and the reaction of the azide with the amine, respectively.

Active Ester Method

In this method, the carboxylic acid of formula (VII) is first converted to an active ester by reacting it with a suitable reagent for producing active esters, after which this active ester is reacted with the amine of formula (VIII).

Formation of the active ester is preferably effected by reacting the carboxylic acid of formula (VII) with, for example, an N-hydroxyimide compound, such as N-hydroxysuccinimide, 1-hydroxybenzotriazole or N-hydroxy-5-norbornene-2,3-dicarboximide. The reaction to form the active ester is preferably effected in the presence of a condensing agent, such as dicyclohexylcarbodiimide or carbonyldiimidazole.

The reaction to form the active ester is also preferably effected in the presence of an inert solvent, the nature of which is not critical, provided that it has no adverse effect upon the reaction. Suitable solvents include, for example: halogenated hydrocarbons, preferably halogenated aliphatic hydrocarbons, such as methylene chloride or chloroform; ethers, such as diethyl ether or tetrahydrofuran; and amides, such as dimethylformamide or dimethylacetamide.

The reaction temperature may vary over a wide range, for example from −10° C. to +25° C. The time required for the reaction may also vary widely, depending upon the nature of the reagents and upon the reaction temperature, but a period of from 30 minutes to 10 hours will normally suffice.

Reaction of this active ester with the amine of formula (VIII) may be carried out with or without intermediate isolation of the active ester. Reaction of the active ester with the amine is preferably effected in the presence of an inert solvent, examples of which are as given for the preparation of the active ester itself. The temperature required for the reaction is not particularly critical and, for this reason, we normally prefer to carry out the reaction at about ambient temperature, although other reaction temperatures may also be employed with equal success. The time required for the reaction will vary widely, but a period of from 30 minutes to 10 hours will normally suffice.

Mixed Acid Anhydride Method

In this method, the carboxylic acid of formula (VII) is first converted to a mixed acid anhydride, and this is then reacted with the amine of formula (VIII).

Preparation of the mixed acid anhydride is effected by reacting the acid of formula (VII) with a suitable reagent, preferably in the presence of an inert solvent. Suitable reagents include: lower alkyl haloformates, such as ethyl chloroformate or isobutyl chloroformate; and di(lower alkyl) cyanophosphonates, such as diethyl cyanophosphonate. Examples of suitable inert solvents include the amides and ethers referred to in relation to the active ester method.

This reaction is preferably effected in the presence of an organic amine, such as triethylamine or N-methylmorpholine. The reaction temperature may vary over a wide range, for example from −10° C. to 25° C. The period required for the reaction may also vary widely, depending upon such factors as the nature of the reagents and the reaction temperature, but a period of from 30 minutes to 5 hours will normally suffice.

Reaction of the resulting mixed acid anhydride with the amine of formula (VIII) is preferably effected in the presence of an inert solvent, the nature of which is not critical, provided that it does not interfere with the reaction. Suitable solvents include the amides and ethers hereinbefore exemplified in relation to the active ester method. The reaction will take place over a wide range of temperatures, but we generally find it convenient to carry out the reaction at a temperature of from 0° C. to about ambient temperature. The time required for the reaction will vary, depending upon many factors, such as the nature of the reagents and the reaction temperature, but a period of from 1 hour to 24 hours will normally suffice.

Condensation Method

In this method, the carboxylic acid of formula (VII) is directly reacted with the amine of formula (VIII). Such a reaction is preferably effected in the presence of a condensing agent, such as dicyclohexylcarbodiimide or carbonyldiimidazole. Otherwise, the reaction conditions and solvents are similar to those already described in relation to the active ester method.

In Method B (Steps B1 and B2), there is shown an alternative method of preparing the compound of formula (I), in which a compound of formula (VII) or a reactive derivative thereof is reacted with a compound of formula (XXVIIIb) to give a compound of formula (Ia); this reaction may be carried out using similar reagents and reaction conditions to those employed in Step A1. The resulting compound of formula (Ia) is then reacted with an amino compound of formula (XXIX), to give the desired compound of formula (I).

The reaction of the compound of formula (Ia) with the compound of formula (XXIX) is preferably effected in the presence of an inert solvent, the nature of which is not critical, provided that it has no adverse effect upon the reaction. Suitable solvents include, for example: ethers, such as diethyl ether, tetrahydrofuran or dioxane; hydrocarbons, especially aromatic hydrocarbons, such as benzene, toluene or xylene; and alcohols, such as methanol or ethanol; of these, the alcohols are preferred. Alternatively, a large excess of the compound of formula (XXIX) can be used as the reaction solvent.

The reaction temperature may vary over a wide range, for example from 0° C. to 150° C., preferably from 0° C. to 100° C. The time required for the reaction may also vary widely, depending upon the nature of the reagents and upon the reaction temperature, but a period of from 30 minutes to 20 hours will normally suffice.

Alternatively, in place of Step B1, the compound of formula (Ia) can be prepared by reacting a compound of formula (IX) (see Method C) with a compound of formula (Xa):

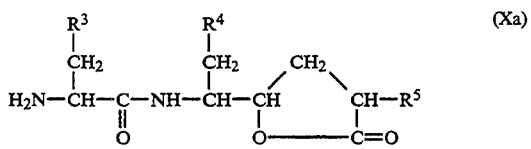

using reagents and reaction conditions similar to those described above in Step A1.

In Method C (Step C1) there is shown an alternative method of preparing the compound of formula (I), in which a compound of formula (IX) or a reactive derivative thereof is reacted with a compound of formula (X) in a similar manner to that described in Step A1. The reaction is a peptide condensation and hence may be carried out using exactly the same reactions and types of reagents as described in relation to Method A.

The compound of formula (VIII), (X) or (XXVIIIb), which is one of the starting materials in the above Methods, may, if desired, be prepared in the form of a corresponding compound in which the amino group is protected. Hence, before using it in the reaction of Method A, Method B or Method C, the protecting group must be removed. The removal of the protecting group may be effected by conventional means and the precise removal reaction chosen will depend upon the nature of the protecting group and is not critical to the present invention.

For example, where the amino-protecting group is a t-butoxycarbonyl group, this group may be removed by treatment with an acid (e.g. a mineral acid, such as hydrochloric acid or hydrofluoric acid, an organic acid, such as trifluoroacetic acid, or a Lewis acid, such as boron trifluoride, preferably in the form of a complex, e.g. the diethyl etherate), optionally in the presence of a cation scavenger (e.g. anisole or thioanisole). Such a reaction is preferably effected in an inert solvent. The nature of the solvent is not critical, provided that it has no adverse effect on the reaction, and examples of suitable solvents include: ethers, such as dioxane; lower alcohols, such as methanol; and amides, such as dimethylformamide. The reaction will take place over a wide range of temperatures, and the precise temperature chosen is not critical to the invention; we generally find it convenient to carry out the reaction at, for example, a temperature of from 0° C. to 30° C. The time required for the reaction may vary widely, depending upon many factors, notably the nature of the reagents and the reaction temperature; however, under the preferred conditions outlined above, a period of from 20 minutes to 1 hour will normally suffice.

When the amino group is protected by an aralkyloxycarbonyl group or other carbonate residue, the protecting group can be removed by catalytic reduction of the protected compound in the presence of hydrogen (for example under a hydrogen pressure of from atmospheric to 14 atmospheres) and in the presence of a suitable hydrogenation catalyst, for example palladium-on-carbon, palladium black or Raney nickel. The reaction is preferably effected in the presence of an inert solvent, the nature of which is not critical, provided that it has no adverse effect on the reaction, and examples of suitable solvents include: lower alcohols, such as methanol or ethanol; and ethers, such as tetrahydrofuran. We generally find it convenient to carry out the reaction at about ambient temperature, although this is not critical. The time required for the reaction may vary widely, depending upon the reaction conditions, but a period of from 1 to 8 hours will normally suffice.

After completion of any of the above reactions or of the final such reaction, the desired compound may be isolated from the reaction mixture by conventional means. For example, one suitable recovery procedure comprises: if necessary, neutralizing the reaction mixture; removing the insoluble residue, if any, by filtration; and then distilling off the solvent to give the desired compound. If necessary, the resulting compound may be further purified by such conventional means as recrystallization, reprecipitation or the various chromatography techniques, such as column chromatography or preparative thin layer chromatography.

Preparation of Starting Materials

The compounds of formulae (VII), (VIII), (IX), (X), (Xa) and (XXVIIIb) are known, or can be prepared without any difficulty according to known methods [for example, as described in Japanese Patent Kokai Publication No. Sho 63-63649, Japanese Patent Kokai Publication No. Sho 62-53952 and Organic Reactions, 8, 28 (1954)]. Alternatively, the preferred (R)-isomer of the compound of formula (IX), that is the compound of formula (IXa) shown below, can be prepared stereoselectively as shown in the reaction scheme of Method D below.

Method D:

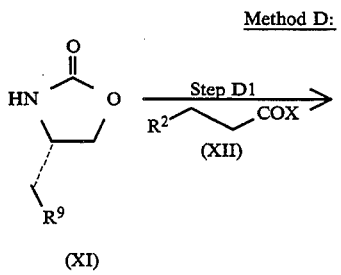

-continued
Method D:

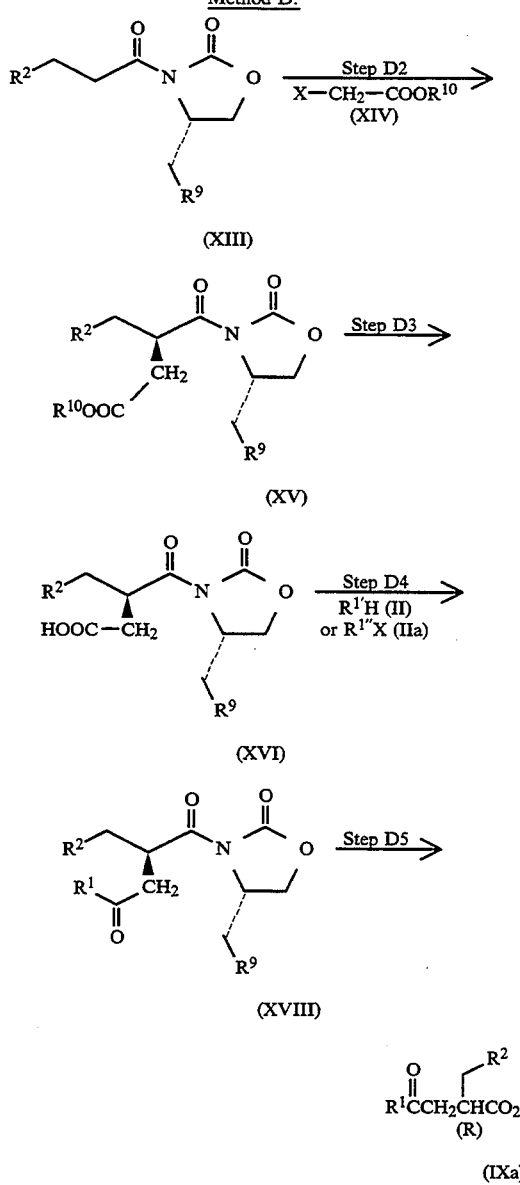

In the above formulae:
$R^1$, $R^{1'}$, $R^{1''}$ and $R^2$ are as defined above;
X represents a halogen atom, preferably a chlorine or bromine atom;
$R^9$ represents a phenyl group or a $C_1$–$C_4$ alkyl group and;
$R^{10}$ represents a $C_1$–$C_4$ alkyl group.

In Step D1 of the above reaction scheme, a compound of formula (XI) is treated with a base (for example butyllithium) to convert it to the corresponding metal salt. This metal salt is then reacted with an acid halide compound of formula (XII) to give the compound of formula (XIII). This compound of formula (XIII) is then reacted, in Step D2, with a base (for example lithium diisopropylamide), after which the resulting compound is reacted stereoselectively with the compound of formula (XIV) to give a compound of formula (XV). This compound of formula (XV) is then converted in Step D3 to the corresponding free acid of formula (XVI), for example by catalytic reduction (which may be as described above in relation to the catalytic hydrogenation employed to remove an amino protecting group, e.g. by treating with hydrogen in the presence of a catalyst such as palladium-on-charcoal) or by hydrolyis by conventional means. In Step D4, this free acid of formula (XVI) is reacted with an amine compound of formula $R^{1'}H$ (II) in the presence of a condensing agent (for example diethyl cyanophosphonate and triethylamine), to give a compound of formula (XVIII) where $R^1$ represents a heterocyclic group attached to the carbonyl group via a nitrogen atom. Alternatively, in Step D4, the free acid of formula (XVI) may be converted to its acid halide by treatment with a halogenating agent, for example thionyl chloride, after which the acid halide is reacted with a compound of formula $R^{1''}$-Mg-X (in which $R^{1''}$ and X are as defined above) in the presence of cadmium chloride, zinc chloride or cuprous chloride, as described in Organic Reactions, 8, 28 (1954), to give a compound of formula (XVIII) where $R^1$ represents a heterocyclic group attached to the carbonyl group via a carbon atom. Finally, in Step D5, this compound of formula (XVIII) is hydrolysed, to give the desired compound of formula (IXa).

Amino acids of formula (XIX):

which may be used as starting materials, can be prepared easily by the procedure summarized in the following reaction scheme of Method E:

Method E

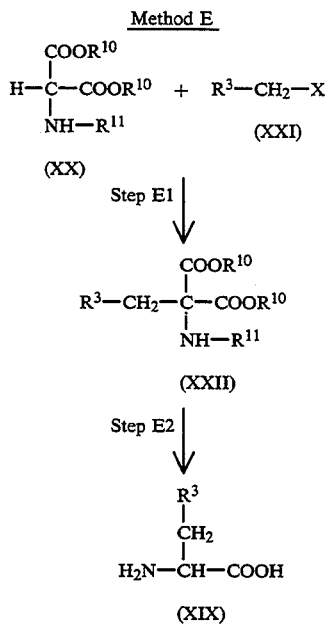

In the above formulae:
$R^3$, $R^{10}$ and X are as defined above; and
$R^{11}$ represents an aliphatic acyl group, preferably containing from 2 to 6 carbon atoms and preferably an alkanoyl group, such as an acetyl, propionyl or butyryl group.

Thus, in Step E1, the compound of formula (XX) is treated with a base (for example an alkali metal hydride, such as sodium hydride), and then the resulting product is reacted with a compound of formula (XXI), to give a compound of formula (XXII). In Step E2, this compound of formula (XXII) is treated with an acid (for example a mineral acid, such as hydrochloric acid), to give a compound of formula (XIX).

A compound of formula (Xa) can be prepared by reacting a compound of formula (XIXa), shown below, which may itself be prepared by protecting the amino group of a compound of formula (XIX)] with a compound of formula (XXVIIIb) in a similar manner to that described in Step A1, followed by removing the amino-protecting group:

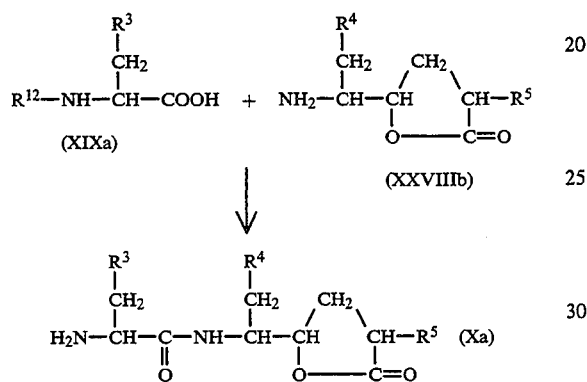

In the above formulae, $R^{12}$ represents an amino-protecting group, and $R^3$, $R^4$ and $R^5$ are as defined above.

Of the compounds of formula (VIII), that isomer which has the preferred configuration, that is to say a compound of formula (VIIIa), can be prepared stereoselectively by the procedure summarized in the following reaction scheme of Method F:

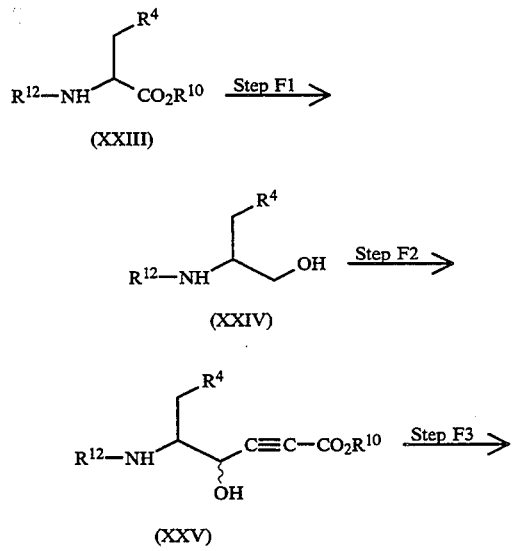

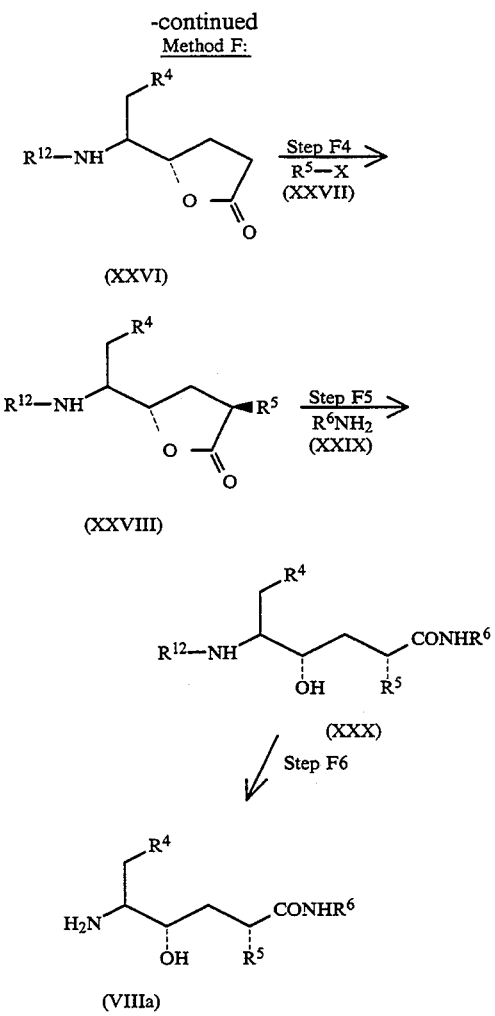

In the above formulae, $R^4$, $R^5$, $R^6$, $R^{10}$, $R^{12}$ and X are as defined above.

Referring to the above reaction scheme, in Step F1, a compound of formula (XXIII) is reduced with a reducing agent, such as sodium borohydride, to give a compound of formula (XXIV). This compound is then, in Step F2, oxidized, for example with a sulfur trioxide-pyridine complex, and then reacted with a lithium (lower alkyl) acetylene carbonate, e.g. at a temperature of from $-78°$ C. to $0°$ C., to form a compound of formula (XXV). In Step F3, this compound is subjected to catalytic reduction, e.g. in the presence of hydrogen and of palladium-on-barium sulfate, and the resulting compound is then heated, in the presence of a catalytic amount of acetic acid, to give a compound of formula (XXVI). In Step F4, this compound of formula (XXVI) is reacted with an alkyl halide of formula $R^5$—X (XXVII) in the presence of lithium diisopropylamide, to give a compound of formula (XXVIII). Finally, this compound of formula (XXVIII) is reacted in Step F5 with an amine compound of formula $R^6NH_2$ (XXIX), to give a compound of formula (XXX), from which an amino-protecting group is removed in Step F6, to give the desired compound of formula (VIIIa).

A compound of formula (XXVIIIb) can be prepared by removing an amino-protecting group from a compound of formula (XXVIII) (see Method F) using any of the reactions described above.

An alternative method of preparing a compound of formula (XXVIII) in which $R^5$ represents an isopropyl group, that is to say a compound of formula (XXVIIIa), is shown in the following reaction scheme of Method G:

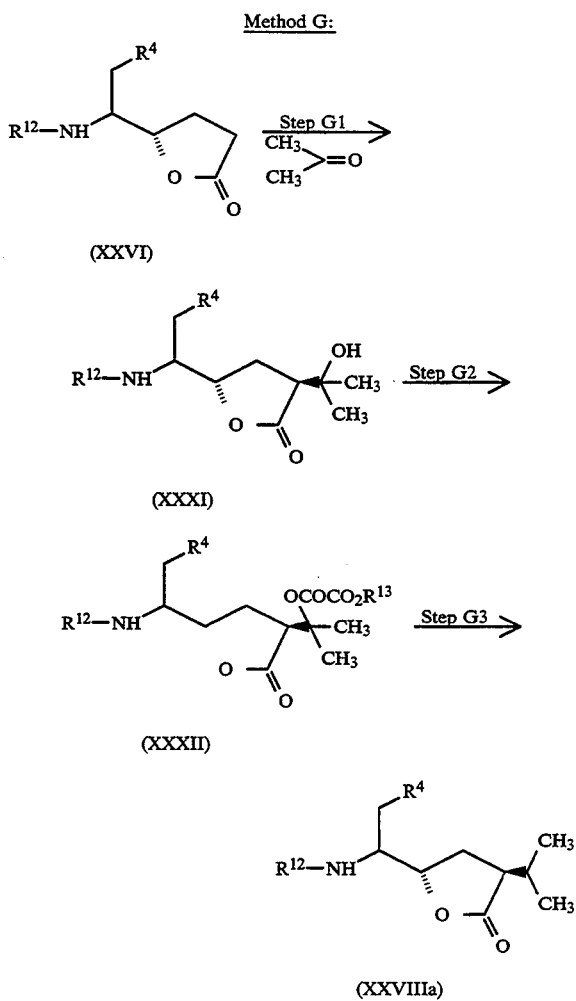

In the above formulae:

$R^4$ and $R^{12}$ are as defined above; and $R^{13}$ represents a $C_1$-$C_4$ alkyl group.

The reaction sequence comprises:

Step G1: reacting a compound of formula (XXVI) (see Method F) with acetone in the presence of a base, such as lithium diisopropylamide, to give a compound of formula (XXXI);

Step G2: reacting the resulting compound with a $C_1$-$C_4$ alkyl oxalyl halide, such as methyl oxalyl chloride, in the presence of a base, such as triethylamine, to give a compound of formula (XXXII); and Step G3: reacting the resulting compound with a trialkyltin hydride, such as tributyltin hydride, to give the desired compound of formula (XXVIIIa).

INHIBITION OF RENIN ACTIVITY

The ability of various compounds of the invention to inhibit the activity of renin was determined according to the following method, which follows essentially the procedure of Kokubu et al. [Hypertension, 5, 191-197 (1983)].

Specifically, each test compound was dissolved in 60% v/v aqueous ethanol. Human renin activity in the presence and absence of each compound was measured using sheep angiotensinogen. The total volume of 1 ml of assay mixture contained 0.1 mole/liter phosphate buffer (pH 7.3), human renin (equivalent to 0.5 ng angiotensin I per ml per minute), sheep angiotensinogen (equivalent to 200 ng angiotensin I), $1 \times 10^{-7}$M of the test compound, 6% v/v ethanol and angiotensinase inhibitors (10 mmole/liter sodium ethylenediaminetetraacetate and 3.4 mmole/liter 8-hydroxyquinoline). The mixture was allowed to react for 10 minutes at 37° C., and then the reaction was stopped by placing the reaction tube in a boiling water bath for 5 minutes. The mixture was then centrifuged and the supernatant (0.05-0.1 ml) was used to assay remaining angiotensin I.

An identical experiment was carried out, as a control, except that the test compound was omitted. From the values obtained were calculated the % inhibition of renin activity achieved by each test compound. The results are shown in the following Table 2, in which the compounds of the invention are identified by the numbers of the Examples given hereafter in which are described their preparation. The values given are the mean of 3 or 4 experiments.

TABLE 2

| Test compound | Inhibitory activity (%) Against Human Renin ($1 \times 10^{-7}$M) |
| --- | --- |
| Compound of Example 1 | 95.2 |
| Compound of Example 2 | 96.0 |
| Compound of Example 3 | 93.1 |
| Compound of Example 4 | 96.9 |
| Compound of Example 5 | 95.6 |
| Compound of Example 6 | 96.1 |
| Compound of Example 8 | 96.2 |
| Compound of Example 11 | 91.6 |
| Compound of Example 14 | 95.7 |
| Compound of Example 16 | 94.8 |

As can be seen from the results in the Table above, the compounds of the present invention have a substantial inhibitory effect on the activity of human renin and are thus useful for the diagnosis, prophylaxis and therapy of renin/angiotensin-induced hypertension in humans and other animals. Furthermore, we have found from blood plasma experiments that the compounds are well absorbed from the digestive tract upon oral administration and this has been supported by tests in marmosets. Moreover, in animal tests using mice and rats, the compounds of the present invention have demonstrated a lower toxicity. All of these results indicate that the compounds of the invention will be of considerable therapeutic and prophylactic value and that, unlike many related compounds proposed previously, they may be administered, in practice, by the oral route, as well as by the more conventional parenteral route.

The compounds of the invention may be formulated in conventional dosage-forms, normally in admixture with a pharmaceutical carrier or diluent, as is well known in the art. For oral administration, the compounds can be formulated, for example, as tablets, capsules, granules, powders or syrups. For parenteral administration, they may be formulated as injections in a suitable liquid or as suppositories. The dosage will vary, depending upon the age, symptoms and body weight of the patient, as well as upon the desired end result; however, for an adult human patient, we would normally anticipate administering a dose of from 0.01 mg to 100 mg/kg body weight per day, which may be administered as a single dose or in divided doses.

The invention is further illustrated by the following Examples, which illustrate the preparation of certain of the compounds of the present invention, and the subsequent Preparations, which illustrate the preparation of some of the starting materials used in the preparation of the compounds of the present invention.

EXAMPLE 1

(2S, 4S, 5S)-5-{N-[2(R)-Benzyl-3-(morpholinocarbonyl)-propionyl]-3-(4-thiazolyl)-L-alanyl}amino-6-cyclohexyl-4-hydroxy-2-isopropyl-N-methylhexanamide

1(a) (2S, 4S, 5S)-5-[N-(t-Butoxycarbonyl)-3-(4-thiazolyl)-L-alanyl-]amino-6-cyclohexyl-4-hydroxy-2-isopropyl-N-methylhexanamide A mixture of 966 mg (2.51 mmole) of (2S, 4S, 5S)-5-(t-butoxycarbonyl)amino-6-cyclohexyl-4-hydroxy-2-isopropyl-L-methylhexanamide (prepared as described in Preparation 3) and 25 ml of a 4N solution of hydrogen chloride in dioxane was stirred at room temperature for 30 minutes. The solvent was then stripped from the mixture by distillation under reduced pressure, and diethyl ether was added to the residue. The resulting mixture was then concentrated by evaporation under reduced pressure. This operation was repeated three times, after which the final residue was dried by evaporation under reduced pressure for 8 hours. At the end of this time, the dried material was suspended in 20 ml of anhydrous tetrahydrofuran, and 752 mg (2.76 mmole) of N-(t-butoxycarbonyl)-3-(4-thiazolyl)-L-alanine were added to the suspension. 0.42 ml (2.77 mmole) of 95% diethyl cyanophosphonate (i.e. diethyl cyanophosphonate of 95% purity) and 0.77 ml (5.52 mmole) of triethylamine were added to the mixture, whilst ice-cooling and under an atmosphere of nitrogen. The mixture was then stirred at room temperature for 6 hours, after which the solvent was removed by distillation under reduced pressure. The resulting residue was purified by medium pressure column chromatography through silica gel (using a 20:1 by volume mixture of methylene chloride and methanol as the eluent) to afford 960 mg (yield 71%) of the title compound as white crystals, melting at 183°–185° C.

$[\alpha]_D^{20} = -40.0°$ (c=0.43, methanol).

Elemental analysis: Calculated for $C_{27}H_{46}N_4O_5S \cdot \frac{1}{2}H_2O$: C, 59.21%; H, 8.65%; N, 10.23%; S, 5.85%. Found: C, 58.79%; H, 8.22%; N, 9.96%; S, 5.59%.

Infrared Absorption Spectrum $(KBr)\nu_{max} cm^{-1}$: 1686, 1640.

Mass spectrum (m/e): 539 (M$^+$+1), 381, 127.

1(b) (2S, 4S, 5S)-5-{N-[2(R)-Benzyl-3-(morpholinocarbonyl)propionyl]-3-(4-thiazolyl) -L-alanyl}amino-6-cyclohexyl-4-hydroxy-2-isopropyl-N-methylhexanamide A mixture of 300 mg (0.56 mmole) of (2S, 4S, 5S)-5-[N-(t-butoxycarbonyl)-3-(4-thiazolyl)-L-alanyl]amino-6-cyclohexyl-4-hydroxy-2-isopropyl-N-methylhexanamide [prepared as described in Example 1(a)] and 5 ml of a 4N solution of hydrogen chloride in dioxane was stirred at room temperature for 30 minutes. The solvent was then removed by distillation under reduced pressure. Diethyl ether was added to the residue, and the mixture was concentrated by evaporation under reduced pressure. This operation was repeated three times. After the final residue had been dried under reduced pressure for 8 hours, the dried material was suspended in 10 ml of anhydrous tetrahydrofuran. 170 mg (0.61 mmole) of 2(R)-benzyl-3-(morpholinocarbonyl)-propionic acid were then added to the suspension. 0.09 ml (0.59 mmole) of 95% diethyl cyanophosphonate and 0.26 ml (1.86 mmole) of triethylamine were then added to the resulting mixture, whilst ice-cooling and under an atmosphere of nitrogen. The mixture was then stirred at room temperature for 8 hours, after which the solvent was removed by distillation under reduced pressure. The resulting residue was purified by preparative thin layer chromatography on silica gel (using a 10:1 by volume mixture of methylene chloride and methanol as the developing solvent), to afford 281 mg (yield 72%) of the title compound as white crystals, melting at 83°–86° C.

$[\alpha]_D^{20} = -38.0°$ (c=0.5, methanol).

Elemental analysis: Calculated for $C_{37}H_{55}N_5O_6S \cdot \frac{1}{2}H_2O$: C, 62.86%; H, 7.98%; N, 9.91%; S, 4.54%. Found: C, 62.82%; H, 8.08%; N, 9.80%; S, 4.52%.

EXAMPLE 2

(2S, 4S, 5S)-5-{N-[2(R)-Benzyl-3-(morpholinocarbonyl)-propionyl]-3-(4-thiazolyl)-L-alanyl}amino-N-butyl-6-cyclohexyl-4-hydroxy-2-isopropylhexanamide

2(a) (2S, 4S, 5S)-5-[N-(t-Butoxycarbonyl)-3-(4-thiazolyl)-L-alanyl-]amino-N-butyl-6-cyclohexyl-4-hydroxy-2-isopropylhexanamide A mixture of 370 mg (0.87 mmole) of (2S, 4S, 5S)-5-(t-butoxycarbonyl)amino-6-cyclohexyl-4-hydroxy-2-isopropyl-N-butylhexanamide (prepared as described in Preparation 4) and 5 ml of a 4N solution of hydrogen chloride in dioxane was stirred at room temperature for 30 minutes. At the end of this time, the solvent was removed by distillation under reduced pressure, and the residue was mixed with diethyl ether. The solvent was once again removed by distillation under reduced pressure. This operation was repeated three times, and the final residue was then dried in vacuo for 8 hours. At the end of this time, the dried material was suspended in 10 ml of anhydrous tetrahydrofuran, and 260 mg (0.96 mmole) of N-(t-butoxycarbonyl)-3-(4-thiazolyl)-L-alanine were added to the suspension. After this, 0.15 ml (0.99 mmole) of 95% diethyl cyanophosphonate and 0.27 ml (1.94 mmole) of triethylamine were added, in that order, to the suspension, whilst ice-cooling and under an atmosphere of nitrogen, after which the mixture was stirred for 6 hours. The reaction mixture was then freed from the solvent by evaporation under reduced pressure, and the resulting residue was purified by medium pressure column chromatography through silica gel (using a 20:1 by volume mixture of methylene chloride and methanol as the eluent) to afford 470 mg (yield 93%) of the title compound as white crystals, melting at 201°–203° C.

$[\alpha]_D^{20} = -43.7°$ (c=1, methanol).

Elemental analysis: Calculated for $C_{30}H_{52}N_4O_5S$: C, 62.04%; H, 9.02%; N, 9.65%; S, 5.52%. Found: C, 62.12%; H, 9.07%; N, 9.74%; S, 5.69%.

2(b) (2S, 4S, 5S)-5-{N-[2(R)-Benzyl-3-(morpholinocarbonyl)propionyl]-3-(4-thiazolyl)-L-alanyl}amino-N-butyl-6-cyclohexyl-4-hydroxy-2-isopropylhexanamide A mixture of 150 mg (0.26 mmole) of (2S, 4S, 5S)-5-[N-(t-butoxycarbonyl)-3-(4-thiazolyl)-N-alanyl]amino-L-butyl-6-cyclohexyl-4-hydroxy-2-isopropylhexanamide [prepared as described in Example 2(a)] and 5 ml of a 4N solution of hydrogen chloride in dioxane was stirred at room temperature for 30 minutes. The solvent was then removed by distillation under reduced pressure, and the resulting residue was mixed with diethyl ether, which was then distilled off under reduced pressure. This operation was repeated three times in total. The final residue was dried in vacuo for 8 hours, and the dried material was suspended in 10 ml of anhydrous tetrahydrofuran. 79 mg (0.29 mmole) of 2(R)-benzyl-3-(morpholinocarbonyl)propionic acid were then added to the suspension. After this, 0.04 ml (0.26 mmole) of 95% diethyl cyanophosphonate and 0.12 ml (0.86 mmole) of triethylamine were added, in that order, to the mixture, whilst ice-cooling and under an atmosphere of nitrogen. The mixture was then stirred for 8 hours, after which the solvent was distilled off under reduced pressure. The resulting residue was purified by preparative thin layer chromatography on silica gel (using a 10:1 by volume mixture of methylene chloride and methanol as the developing solvent), to afford 138 mg (yield 72%) of the title compound as white crystals, melting at 161°–163° C.

$[\alpha]_D^{20} = -40.4°$ (c=0.5, methanol).

Elemental analysis: Calculated for $C_{40}H_{61}N_5O_6S \cdot \frac{1}{2}H_2O$: C, 64.14%; H, 8.34%; N, 9.35%; S, 4.28%. Found: C, 64.39%; H, 8.07%; N, 9.35%; S, 4.29%.

EXAMPLE 3

(2S, 4S, 5S)-5-{N-[2(R)-(4-Methoxybenzyl)-3-(morpholinocarbonyl)propionyl]-3-(4-thiazolyl)-L-alanyl}amino-6-cyclohexyl-4-hydroxy-2-isopropyl-N-methylhexanamide The procedure described in Example 1(b) was repeated, but using 200 mg (0.37 mmole) of (2S, 4S, 5S)-5-[N-(t-butoxycarbonyl)-3-(4-thiazolyl)-L-alanyl]amino-6-cyclohexyl-4-hydroxy-2-isopropyl-N-methylhexanamide [prepared as described in Example 1(a)] and 137 mg (0.45 mmole) of 2(R)-(4-methoxybenzyl)-3-(morpholinocarbonyl)propionic acid, to afford 188 mg (yield 70%) of the title compound as white crystals, melting at 128°–130° C.

$[\alpha]_D^{20} = -37.6°$ (c=0 5, methanol).

Elemental analysis: Calculated for $C_{38}H_{57}N_5O_7S \cdot H_2O$: C, 61.18%; H, 7.97%; N, 9.39%; S, 4.30%. Found: C, 61.43%; H, 7.83%; N, 9.31%; S, 4.21%.

Mass spectrum (m/e): 728 (M+ +1), 290, 121.

EXAMPLE 4

2S, 4S, 5S)-N-Butyl-6-cyclohexyl-4-hydroxy-2-isopropyl-5-{N-[2(R)-(4-methoxybenzyl-3-(morpholinocarbonyl-prioionyl]-3-(4-thiazolyl)-L-alanyl}aminohexanamide The procedure described in Example 2(b) was repeated, but using 300 mg (0.52 mmole) of (2S, 4S, 5S)-5-N-(t-butoxycarbonyl)-3-(4-thiazolyl)-L-alanyl]amino-N-butyl-6-cyclohexyl-4-hydroxy-2-isopropylhexanamide [prepared as described in Example 2(a)] and 175 mg (0.57 mmole) of 2(R)-(4-methoxybenzyl)-3-(morpholinocarbonyl)propionic acid, to afford 332 mg (yield 83%) of the title compound as white crystals, melting at 152°–154° C.

$[\alpha]_D^{20} = -37.4°$ (c=0.5, methanol).

Elemental analysis: Calculated for $C_{41}H_{63}N_5O_7S$: C, 63.95%; H, 8.25%; N, 9.09%; S, 4.16%. Found: C, 63.66%; H, 8.43%; N, 9.10%; S, 4.22%.

EXAMPLE 5

(2R, 4S, 5S)-5-{N-[2(R)-Benzyl-3-(morpholinocarbonyl)-propionyl]-3-(4-thiazolyl)-L-alanyl}amino-6-cyclohexyl-4-hydroxy-2,N-dimethylhexanamide

5(a) (2R, 4S, 5S)-5-[N-(t-Butoxycarbonyl)-3-(4-thiazolyl)-L-alanyl]amino-6-cyclohexyl-4-hydroxy-2, N-dimethylhexanamide A mixture of 200 mg (0.56 mmole) of (2R, 4S, 5S)-5-(t-butoxycarbonyl)amino-6-cyclohexyl-4-hydroxy-2,N-dimethylhexanamide (prepared as described in Preparation 5) and 4 ml of a 4N solution of hydrogen chloride in dioxane was stirred at room temperature for 30 minutes. At the end of this time, the solvent was removed by distillation under reduced pressure, and the resulting residue was mixed with benzene; the solvent was then removed by distillation under reduced pressure. This operation was repeated three times in total. After drying the final residue in vacuo for 8 hours, the dried material was suspended in 10 ml of anhydrous tetrahydrofuran. 150 mg (1.68 mmole) of N-(t-butoxycarbonyl)-3-(4-thiazolyl)-L-alanine were then added to the suspension. After this, 0.1 ml (0.67 mmole) of 95% diethyl cyanophosphonate and 0.23 ml (1.68 mmole) of triethylamine were added to the mixture, whilst ice-cooling and under an atmosphere of nitrogen. The mixture was then stirred for 15 hours. At the end of this time, the reaction solvent was stripped from the mixture by distillation under reduced pressure and the residue was mixed with water. The precipitate which deposited was collected by filtration and washed with water. It was then dissolved in methylene chloride and the resulting solution was dried over anhydrous magnesium sulfate. The solvent was then removed by distillation under reduced pressure, to afford 260 mg of the title compound as a pale yellow powder, melting at 158°–160° C.

Elemental analysis: Calculated for $C_{25}H_{42}N_4O_5S$: C, 58.80%; H, 8.29%; N, 10.97%; S, 6.28%. Found: C, 58.86%; H, 8.41%; N, 10.67%; S, 6.25%.

5(b) (2R, 4S, 5S)-5-{N-[2(R)-Benzyl-3-(morpholinocarbonyl)propionyl]-3-(4-thiazolyl)-L-alanyl}amino-6-cyclohexyl-4-hydroxy-2,N-dimethylhexanamide A mixture of 110 mg (0.215 mmole) of (2R, 4S, 5S)-5-[N-(t-butoxycarbonyl)-3-(4-thiazolyl)-L-alanyl]amino-6-cyclohexyl-4-hydroxy-2,N-dimethylhexanamide [prepared as described in step (a) above], 2 ml of methanol and 2 ml of a 4N solution of hydrogen chloride in dioxane was stirred at room temperature for 30 minutes. At the end of this time, the solvent was removed by distillation under reduced pressure. The residue was mixed with benzene and the solvent was stripped from the mixture by distillation under reduced pressure. After this operation had been repeated three times, the final residue was dried in vacuo for 8 hours. The dried material was then suspended in 8 ml of anhydrous tetrahydrofuran, and 59.6 mg (0.215 mmole) of 2(R)-benzyl-3-(morpholinocarbonyl)propionic acid were added to the suspension. 0.042 ml (0.258 mmole) of 95% diethyl cyanophosphonate and 0.12 ml (0.86 mmole) of triethylamine were then added to the mixture, and the resulting mixture was stirred for 18 hours. At the end of this time, the reaction mixture was concentrated by distillation under reduced pressure, and the residue was purified by preparative thin layer chromatography on silica gel (using a 10:1 by volume mixture of methylene chloride and methanol as the developing solvent), to afford 50 mg of the title compound as a white powder.

Elemental analysis: Calculated for $C_{35}H_{51}N_5O_6 \cdot S \cdot 3H_2O$: C, 58.07%; H, 7.94%; N, 9.67%; S, 4.43%. Found: C, 57.71%; H, 7.56%; N, 9.19%; S, 4.40%.

EXAMPLE 6

2R, 4S, 5S)-5-{N-[2(R)-Benzyl-3-(morpholinocarbonyl)-propionyl]-3-(4-thiazolyl)-L-alanyl}amino-N-butyl-6-cyclohexyl-4-hydroxy-2-methylhexanamide

6(a) (2R, 4S, 5S)-5-[N-(t-Butoxycarbonyl)-3-(4-thiazolyl)-L-alanyl-]amino-N-butyl-6-cyclohexyl-4-hydroxy-2-methylhexanamide A mixture of 220 mg (0.552 mmole) of (2R, 4S, 5S)-5-(t-butoxycarbonyl)amino-L-butyl-6-cyclohexyl-4-hydroxy-2-methylhexanamide (prepared as described in Preparation 6) and 5 ml of a 4N solution of hydrogen chloride in dioxane was stirred at room temperature for 30 minutes. The solvent was then removed by distillation under reduced pressure, after which the residue was mixed with benzene; the mixture was then again concentrated by distillation under reduced pressure. This operation was repeated three times in total. The final residue was dried in vacuo for 8 hours. At the end of this time, the dried material was suspended in 10 ml of anhydrous tetrahydrofuran, and 0.15 g (0.552 mmole) of N-(t-butoxycarbonyl)-3-(4-thiazolyl)-L-alanine was added to the resulting suspension. 0.11 ml (0.662 mmole) of 95% diethyl cyanophosphonate and 0.23 ml of triethylamine were then added to the mixture, whilst ice-cooling and under an atmosphere of nitrogen. The resulting mixture was stirred for 14 hours. At the end of this time, the reaction mixture was concentrated by distillation under reduced pressure, and the resulting residue was mixed with water. The precipitate which deposited was collected by filtration and washed with water. It was then dissolved in methylene chloride. The resulting solution was dried over anhydrous magnesium sulfate, and the solvent was then removed by distillation under reduced pressure. The residue was triturated with diisopropyl ether to afford 243 mg of the title compound as a pale yellow powder, melting at 172°–174° C.

Elemental analysis: Calculated for $C_{28}H_{48}N_4O_5S$: C, 60.84%; H, 8.75%; N, 10.14%; S, 5.80%. Found: C, 60.51%; H, 8.75%; N, 10.13%; S, 6.02%.

6(b) (2R, 4S, 5S)-5-{N-[2(R)-Benzyl-3-(morpholinocarbonyl)propionyl]-3-(4-thiazolyl)-L-alanyl}amino-N-butyl-6-cyclohexyl-4-hydroxy-2-methylhexanamide A mixture of 230 mg (0.416 mmole) of (2R, 4S, 5S)-5-[N-(t-butoxycarbonyl)-3-(4-thiazolyl)-L-alanyl]amino-N-butyl-6-cyclohexyl-4-hydroxy-2-methylhexanamide [prepared as described in Example 6(a)] and 5 ml of a 4N solution of hydrogen chloride in dioxane was stirred at room temperature for 30 minutes. The mixture was then freed from the solvent by distillation under reduced pressure, and the residue was mixed with benzene; the solvent was then removed by distillation under reduced pressure. This operation was repeated three times in total. After the final residue had been dried in vacuo for 8 hours, it was suspended in 15 ml of anhydrous tetrahydrofuran. 120 mg (0.416 mole) of 2(R)-benzyl[-3-(morpholinocarbonyl)propionic acid were then added to the suspension. 82 μl (0.499 mmole) of 95% diethyl cyanophosphonate and 0.23 ml (1.664 mmole) of triethylamine were then added to the mixture, whilst ice-cooling and under an atmosphere of nitrogen, after which the mixture was stirred for 15 hours. At the end of this time, the reaction mixture was concentrated by distillation under reduced pressure, and the resulting residue was mixed with water to deposit a precipitate. This was collected by filtration and washed with water. The precipitate was then dissolved in methylene chloride and the solution was dried over anhydrous magnesium sulfate. The solvent then was removed by distillation under reduced pressure and the residue was triturated with diisopropyl ether to afford 138 mg of the title compound as a pale yellow powder, melting at 162°–163° C.

Elemental analysis: Calculated for $C_{38}H_{57}N_5O_6 \cdot S \cdot 0.5H_2O$: C, 63.31%; H, 8.11%; N, 9.71%; S, 4.45%. Found: C, 63.30%; H, 8.06%; N, 9.92%; S, 4.65%.

EXAMPLE 7

(2R, 4S, 5S)-N-Butyl-6-cyclohexyl-4-hydroxy-5-{N-[2(R)-(4-methoxybenzyl)-3-(morpholinocarbonyl)propionyl]-3-(4-thiazolyl)-L-alanyl}amino-2-methylhexanamide The procedure described in Example 6(b) was repeated, but using 200 mg (0.36 mmole) of (2R, 4S, 5S)-5-[N-(t-butoxycarbonyl)-3-(4-thiazolyl)-L-alanyl]amino-N-butyl-6-cyclohexyl-4-hydroxy-2-methylhexanamide [prepared as described in Example 6(a)] and 110 mg (0.36 mmole) of 2(R)-(4-methoxybenzyl)-3-(morpholinocarbonyl)propionic acid, to afford 158 mg of the title compound as a white powder, melting at 130°–132° C.

Elemental analysis: Calculated for $C_{39}H_{59}N_5O_7S$: C, 63.13%; H, 8.02%; N, 9.44%; S, 4.32%. Found: C, 62.81%; H, 8.11%; N, 9.29%; S, 5.06%.

EXAMPLE 8

(2R, 4S, 5S)-5-{N-[2(R)-Benzyl-3-(N-benzyl-N-methylaminocarbonyl)propionyl]-3-(4-thiazolyl)-L-alanyl}-amino-N-butyl-6-cyclohexyl-4-hydroxy-2-methylhexanamide The procedure described in Example 6(b) was repeated, but using 170 mg (0.308 mmole) of (2R, 4S, 5S)-5-[N-(t-butoxycarbonyl)-3-(4-thiazolyl)-N-alanyl-]amino-L-butyl-6-cyclohexyl-4-hydroxy-2-methylhexanamide [prepared as described in Example 6(a)] and 96 mg (0.308 mmole) of 2(R)-benzyl-3-(N-benzyl-N-methylaminocarbonyl)propionic acid, to afford 148 mg of the title compound as a white powder, melting at 111°–113° C.

Elemental analysis: Calculated for $C_{42}H_{59}N_5O_5S$: C, 67.62%; H, 7.97%; N, 9.39%; S, 4.30%. Found: C, 67.33%; H, 8.04%; N, 9.53%; S, 4.30%.

EXAMPLE 9

(2R, 4S, 5S)-5-{N-[2(R)-Benzyl-3-(N-cyclohexyl-N-methylaminocarbonyl)-propionyl]-3-(4-thiazonyl)-L-alanyl}amino-N-butyl-6-cyclohexyl-4-hydroxy-2-methylhexanamide The procedure described in Example 6(b) was repeated, but using 170 mg (0.31 mmole) of (2R, 4S, 5S)-5-[N-(t-butoxycarbonyl)-3-(4-thiazolyl)-L-alanyl]amino-N-butyl-6-cyclohexyl-4-hydroxy-2-methylhexanamide [prepared as described in Example 6(a)] and 94 mg (0.308 mmole) of 2(R)-benzyl-3-(N-cyclohexyl-N-methylaminocarbonyl)propionic acid, to afford 149 mg of the title compound as a white powder, melting at 116°–118° C.

Elemental analysis: Calculated for $C_{41}H_{63}N_5O_5S$: C, 66.72%; H, 8.60%; N, 9.49%; S, 4.34%. Found: C, 66.10%; H, 8.59%; N, 9.57%; S, 4.84%.

EXAMPLE 10

(2R, 4S, 5S)-5-{N-[2(R)-Benzyl-3-(morpholinocarbonyl)-propionyl]-3-(4-thiazolyl)-L-alanyl}amino-6-cyclohexyl-N-hexyl-4-hydroxy-2-methylhexanamide

10(a) (2R, 4S, 5S)-5-[N-(t-Butoxycarbonyl)-3-(4-thiazolyl)-L-alanyl]amino-6-cyclohexyl-N-hexyl-4-hydroxy-2-methylhexanamide A mixture of 412 mg (0.96 mmole) of (2R, 4S, 5S)-5-(t-butoxycarbonyl)amino-6-cyclohexyl-N-hexyl-4-hydroxy-2-methylhexanamide (prepared as described in Preparation 7) and 8.0 ml of a 4N solution of hydrogen chloride in dioxane was stirred at room temperature for 30 minutes. At the end of this time, the reaction mixture was freed from the solvent by distillation under reduced pressure, and the residue was mixed with benzene. The solvent was then removed by distillation under reduced pressure. This operation was repeated three times in total, and the final residue was dried in vacuo for 8 hours. The dried material was then suspended in 50 ml of anhydrous tetrahydrofuran, and 289 mg (1.06 mmole) of N-(t-butoxycarbonyl)-3-(4-thiazolyl)-L-alanine were added to the resulting suspension. 0.17 ml (1.06 mmole) of 95% diethyl cyanophosphonate and 0.6 ml (4.3 mmole) of triethylamine were then added, in that order, whilst ice-cooling and under an atmosphere of nitrogen, to the resulting mixture, and the mixture was stirred for 15 hours. At the end of this time, the reaction mixture was concentrated by distillation under reduced pressure, after which the residue was mixed with water and the crystals which deposited were collected by filtration. The crystals were then dissolved in methylene chloride and dried over anhydrous magnesium sulfate, after which the solvent was removed by distillation under reduced pressure. The resulting residue was triturated with diisopropyl ether to afford 465 mg of the title compound as a white powder, melting at 156°–158° C.

10(b) (2R, 4S, 5S)-5-{N-[2(R)-Benzyl-3-(morpholinocarbonyl)propionyl]-3-(4-thiazolyl)-L-alanyl}amino-6-cyclohexyl-N-hexyl-4-hydroxy-2-methylhexanamide The procedure described in Example 6(b) was repeated, but using 200 mg (0.344 mmole) of (2R, 4S, 5S)-5-[N-(t-butoxycarbonyl)-3-(4-thiazolyl)-N-alanyl]amino-6-cyclohexyl-L-hexyl-4-hydroxy-2-methylhexanamide [prepared as described in Example 10(a)] and 105 mg (0.38 mmole) of 2(R)-benzyl-3-(morpholinocarbonyl)propionic acid, to afford 110 mg of the title compound as a white powder.

Elemental analysis: Calculated for $C_{40}H_{61}N_5O_6S$: C, 64.92%; H, 8.31%; N, 9.46%; S, 4.33%. Found: C, 64.26%; H, 8.31%; N, 9.50%; S, 4.55%.

EXAMPLE 11

(2R, 4S, 5S)-N-Butyl-6-cyclohexyl-4-hydroxy-5-{N-[2(R)-(4-methoxybenzyl)-3-(N-benzyl-N-methylaminocarbonyl)-propionyl]-3-(4-thiazolyl)-L-alanyl}amino-2-methylhexanamide The procedure described in Example 6(b) was repeated, but using 150 mg (0.27 mmole) of (2R, 4S, 5S)-5-[N-(t-butoxycarbonyl)-3-(4-thiazolyl)-L-alanyl]amino-N-butyl-6-cyclohexyl-4-hydroxy-2-methylhexanamide [prepared as described in Example 6(a)] and 92 mg (0.27 mmole) of 2(R)-(4-methoxybenzyl)-3-(N-benzyl-N-methylaminocarbonyl)propionic acid, to afford 146 mg of the title compound as a white powder, melting at 112°–114° C.

Elemental analysis: Calculated for $C_{43}H_{61}N_5O_6S$: C, 66.55%; H, 7.92%; N, 9.02%; S, 4.13%. Found: C, 66.31%; H, 7.74%; N, 9.16%; S, 4.01%.

EXAMPLE 12

(2R, 4S, 5S)-N-Butyl-6-cyclohexyl-4-hydroxy-5-{N-[2(R)-(4-methoxybenzyl)-3-(4-methylpiperazinocarbonyl)-propionyl]-3-(4-thiazolyl)-L-alanyl}amino-2-methylhexanamide The procedure described in Example 6(b) was repeated, but using 150 mg (0.27 mmole) of (2R, 4S, 5S)-5-N-(t-butoxycarbonyl)-3-(4-thiazolyl)-L-alanyl]amino-N-butyl-6-cyclohexyl-4-hydroxy-2-methylhexanamide prepared as described in Example 6(a)] and 93 mg (0.27 mmole) of 2(R)-(4-methoxybenzyl)-3-(4-methylpiperazinocarbonyl)propionic acid, to afford 32 mg of the title compound as a white powder, melting at 125°–126° C.

Elemental analysis: Calculated for $C_{40}H_{62}N_6O_6S$: C, 63.63%; H, 8.28%; N, 11.13%; S, 4.25%. Found: C, 63.29%; H, 8.01%; N, 10.98%; S, 3.98%.

EXAMPLE 13

(2R, 4S, 5S)-N-Butyl-6-cyclohexyl-4-hydroxy-5-{N-[2(R)-(4-methoxybenzyl)-3-(piperidinocarbonyl)propionyl]-3-(4-thiazolyl)-L-alanyl}amino-2-methylhexanamide The procedure described in Example 6(b) was repeated, but using 150 mg (0.27 mmole) of (2R, 4S, 5S)-5-[N-(t-butoxycarbonyl)-3-(4-thiazolyl)-L-alanyl]amino-N-butyl-6-cyclohexyl-4-hydroxy-2-methylhexanamide [prepared as described in Example 6(a)] and 86 mg (0.28 mmole) of 2(R)-(4-methoxybenzyl)-3-(piperidinocarbonyl)propionic acid, to afford 47 mg of the title compound as a white powder, melting at 120°–122° C.

Elemental analysis: Calculated for $C_{40}H_{61}N_5O_6S$: C, 64.93%; H, 8.31%; N, 9.46%; S, 4.33%. Found: C, 64.75%; H, 8.56%; N, 9.23%; S, 4.19%.

EXAMPLE 14

(2R, 4S, 5S)-5-{N-[2(R)-Benzyl-3-(N-benzyl-N-methylaminocarbonyl)propionyl]-3-(4-thiazolyl)-L-alanyl}-amino-6-cyclohexyl-4-hydroxy-2,N-dimethylhexanamide The procedure described in Example 5(b) was repeated, but using 250 mg (0.49 mmole) of (2R, 4S, 5S)-5-[N-(t-butoxycarbonyl)-3-(4-thiazolyl)-L-alanyl]amino-6-cyclohexyl-4-hydroxy-2,N-dimethylhexanamide [prepared as described in Example 5(a)] and 156 mg (0.5 mmole) of 2(R)-benzyl-3-(N-benzyl-N-methylaminocarbonyl)propionic acid, to afford 172 mg of the title compound as white crystals, melting at 121°–123° C.

Elemental analysis: Calculated for $C_{39}H_{53}N_5O_5S \cdot \frac{1}{2}H_2O$: C, 65.74%; H, 7.64%; N, 9.83%; S, 4.50%. Found: C, 65.77%; H, 7.47%; N, 9.90%; S, 4.24%.

EXAMPLE 15

(2S, 4S, 5S)-5-{N-[2(R)-Benzyl-3-(N-benzyl-N-methylaminocarbonyl)propionyl]-3-(4-thiazolyl-L-alanyl}-amino-6-cyclohexyl-4-hydroxy-2-isopropyl-N-methylhexanamide The procedure described in Example 1(b) was repeated, but using 260 mg (0.48 mmole) of (2S, 4S, 5S)-5-[N-(t-butoxycarbonyl)-3-(4-thiazolyl)-L-alanyl]amino-56-cyclohexyl-4-hydroxy-2-isopropyl-N-methylhexanamide [prepared as described in Example 1(a)] and 150 mg (0.48 mmole) of 2(R)-benzyl-3-(N-benzyl-N-methylaminocarbonyl)propionic acid, to afford 190 mg of the title compound as a white powder, melting at 125°–127° C.

Elemental analysis: Calculated for $C_{41}H_{57}N_5O_5S$: C, 67.27%; H, 7.85%; N, 9.57%; S, 4.38%. Found: C, 67.02%; H, 7.92%; N, 9.48%; S, 4.17%.

EXAMPLE 16

(2S, 4S, 5S)-5-{N-[2(R)-Benzyl-3-(N-benzyl-N-methylaminocarbonyl)propionyl]-3-(4-thiazolyl)-L-alanyl}amino-N-butyl-6-cyclohexyl-4-hydroxy-2-isopropylhexanamide The procedure described in Example 2(b) was repeated, but using 280 mg (0.48 mmole) of (2S, 4S, 5S)-5-[N-(t-butoxycarbonyl)-3-(4-thiazolyl )-L-alanyl]amino-N-butyl-6-cyclohexyl-4-hydroxy-2-isopropylhexanamide [prepared as described in Example 2(a)] and 150 mg (0.48 mmole) of 2(R)-benzyl-3-(N-benzyl-N-methylaminocarbonyl)propionic acid, to afford 187 mg of the title compound as a white powder, melting at 155°–156° C.

Elemental analysis: Calculated for $C_{44}H_{63}N_5O_5S \cdot \frac{1}{2}H_2O$: C, 67.49%; H, 8.24%; N, 8.94%; S, 4.09%. Found: C, 67.74%; H, 8.17%; N, 8.93%; S, 4.08%.

EXAMPLE 17

(2R, 4S, 5S)-5-{N-[2(R)-Benzyl-3-(N-benzyl-N-methylaminocarbonyl)propionyl]-3-(4-thiazolyl)-L-alanyl}-amino-6-cyclohexyl-4-hydroxy-N-isobutyl-2-methylhexanamide

17(a) (2R, 4S, 5S)-5-[N-(t-Butoxycarbonyl)-3-(4-thiazolyl)-L-alanyl]amino-6-cyclohexyl-4-hydroxy-N-isobutyl-2-methylhexanamide The procedure described in Example 5(a) was repeated, but using 300 mg (0.753 mmole) of (2R, 4S, 5S)-5-(t-butoxycarbonyl)amino-6-cyclohexyl-4-hydroxy-N-isobutyl-2-methylhexanamide (prepared as described in Preparation 17) and 210 mg (0.753 mmole) of 5-(t-butoxycarbonyl)-3-(4-thiazolyl)-L-alanine, to afford 320 mg of the title compound as a colorless powder, melting at 178°–180° C.

17(b) (2R, 4S, 5S)-5-{N-[2(R)-Benzyl-3-(N-benzyl-N-methylaminocarbonyl)propionyl]-3-(4-thiazolyl)-L-alanyl}amino-6-cyclohexyl-4-hydroxy-N-isobutyl-2-methylhexanamide The procedure described in Example 6(b) was repeated, but using 300 mg (0.543 mmole) of (2R, 4S, 5S)-5-[N-(t-butoxycarbonyl)-3-(4-thiazolyl)-L-alanyl]amino-6-cyclohexyl-4-hydroxy-N-isobutyl-2-methylhexanamide [prepared as described in Example 17(a)] and 170 mg (0.543 mmole) of 2(R)-benzyl-3-(N-benzyl-N-methylaminocarbonyl)propionic acid, to afford 216 mg of the title compound as a colorless powder, melting at 118°–120° C.

Elemental analysis: Calculated for $C_{42}H_{59}N_5O_5S$: C, 67.62%; H, 7.97%; N, 9.39%; S, 4.30%. Found: C, 67.50%; H, 8.16%; N, 9.18%; S, 4.13%.

EXAMPLE 18

(2R, 4S, 5S)-5-{N-[2(R)-Benzyl-3-(N-benzyl-N-methylaminocarbonyl)propionyl]-3-(4-thiazolyl)-L-alanyl}-amino-6-cyclohexyl-4-hydroxy-2-methyl-N-propylhexanamide

18(a) (2R, 4S, 5S)-5-[N-(t-Butoxycarbonyl)-3-(4-thiazolyl)-L-alanyl]amino-6-cyclohexyl-4-hydroxy-2-methyl-N-propylhexanamide The procedure described in Example 5(a) was repeated, but using 280 mg (0.728 mmole) of (2R, 4S, 5S)-5-(t-butoxycarbonyl)amino-6-cyclohexyl-4-hydroxy-2-methyl-N-propylhexanamide (prepared as described in Preparation 18) and 204 mg (0.75 mmole) of N-(t-butoxycarbonyl)-3-(4-thiazolyl)-L-alanine, to afford 306 mg of the title compound as colorless crystals, melting at 182°–184° C.

18(b) (2R, 4S, 5S)-5-{N-[2(R)-Benzyl-3-(N-benzyl-N-methylaminocarbonyl)propionyl]-3-(4-thiazolyl)-L-alanyl}amino-6-cyclohexyl-4-hydroxy-2-methyl-N-propylhexanamide The procedure described in Example 6(b) was repeated, but using 252 mg (0.468 mmole) of (2R, 4S, 5S)-5-[N-(t-butoxycarbonyl)-3-(4-thiazolyl)-L-alanyl]amino-6-cyclohexyl-4-hydroxy-2-methyl-N-propylhexanamide [prepared as described in Example 18(a)] and 152 mg (0.488 mmole) of 2(R)-benzyl-3-(N-benzyl-N-methylaminocarbonyl)propionic acid, to afford 111 mg of the title compound as a colorless powder, melting at 115°–118° C.

Elemental analysis: Calculated for $C_{41}H_{57}N_5O_5S$: C, 67.27%; H, 7.85%; N, 9.57%; S, 4.38%. Found: C, 66.97%; H, 8.10%; N, 9.30%; S, 4.42%.

EXAMPLE 19

(2R, 4S, 5S)-5-{N-[2(R)-Benzyl-3-(N-benzyl-N-methylaminocarbonyl)propionyl]-3-(4-thiazolyl)-L-alanyl}-amino-6-cyclohexyl-N-ethyl-4-hydroxy-2-methylhexanamide

19(a) (2R, 4S, 5S)-5-[N-(t-Butoxycarbonyl)-3-(4-thiazolyl)-L-alanyl]amino-6-cyclohexyl-N-ethyl-4-hydroxy-2-methylhexanamide The procedure described in Example 5(a) was repeated, but using 321 mg (0.87 mmole) of (2R, 4S, 5S)-5-(t-butoxycarbonyl)amino-6-cyclohexyl-H-ethyl-4-hydroxy-2-methylhexanamide (prepared as described in Preparation 19) and 242 mg (0.89 mmole) of N-(t-butoxycarbonyl)-3-(4-thiazolyl)-L-alanine, to afford 344 mg of the title compound as white crystals, melting at 179°–181° C.

19(b) (2R, 4S, 5S)-5-{N-[2(R)-Benzyl-3-(N-benzyl-N-methylaminocarbonyl)propionyl]-3-(4-thiazolyl)-L-alanyl}amino-6-cyclohexyl-N-ethyl-4-hydroxy-2-methylhexanamide The procedure described in Example 6(b) was repeated, but using 325 mg (0.62 mmole) of (2R, 4S, 5S)-5-[N-(t-butoxycarbonyl)-3-(4-thiazolyl)-L-alanyl]amino-6-cyclohexyl-N-ethyl-4-hydroxy-2-methylhexanamide [prepared as described in Example 19(a)] and 200 mg (0.64 mmole) of 2(R)-benzyl-3-(N-benzyl-N-methylaminocarbonyl)propionic acid, to afford 129 mg of the title compound as white crystals, melting at 148°–150° C.

Elemental analysis: Calculated for $C_{40}H_{55}N_5O_5S$: C, 66.92%; H, 7.72%; N, 9.75%; S, 4.47%. Found: C, 66.74%; H, 7.64%; N, 9.68%; S, 4.30%.

EXAMPLE 20

(2R, 4S, 5S)-5-{N-[2(R)-Benzyl-3-(N-benzyl-N-methylaminocarbonyl)propionyl]-3-(4-thiazolyl)-L-alanyl}-amino-6-cyclohexyl-4-hydroxy-N-isopropyl-2-methylhexanamide

20(a) (2R, 4S, 5S)-5-[N-(t-Butoxycarbonyl)-3-(4-thiazolyl)-L-alanyl]amino-6-cyclohexyl-4-hydroxy-N-isopropyl-2-methylhexanamide The procedure described in Example 5(a) was repeated, but using 180 mg (0.47 mmole) of (2R, 4S, 5S)-5-(t-butoxycarbonyl)amino-6-cyclohexyl-4-hydroxy-N-isopropyl-2-methylhexanamide {prepared by reacting (3R, 5S)-5-[(1S)-1-(t-butoxycarbonylamino)-2-cyclohexylethyl]-3-methyldihydrofuran-2(3H)-one, as described in Preparation 2, with isopropylamine according to the procedure described in Preparation 19}, to afford 185 mg of the title compound, melting at 185°–187° C.

20(b) (2R, 4S, 5S)-5-{N-[2(R)-Benzyl-3-N-benzyl-N-methylaminocarbonyl)propionyl]-3-(4-thiazolyl)-L-alanyl}amino-6-cyclohexyl-4-hydroxy-N-isopropyl-2-methylhexanamide The procedure described in Example 6(b) was repeated, but using 170 mg (0.32 mmole) of (2R, 4S, 5S)-5-[N-(t-butoxycarbonyl)-3-(4-thiazolyl)-L-alanyl]amino-6-cyclohexyl-4-hydroxy-N-isopropyl-2-methyihexanamide [prepared as described in Example 20(a)] and 98.4 mg (0.32 mmole) of 2(R)-benzyl-3-(N-benzyl-N-methylaminocarbonyl)propionic acid, to afford 108 mg of the title compound, melting at 142°–144° C.

Elemental analysis: Calculated for $C_{41}H_{57}N_5O_5S$: C, 67.27%; H, 7.85%; N, 9.57%; S, 4.38%. Found: C, 67.08%; H, 7.90%; N, 9.44%; S, 4.22%.

EXAMPLE 21

(2R, 4S, 5S)-5-{N-[2(R)-Benzyl-3-(morpholinocarbonyl)-propionyl]-3-(4-thiazolyl)-L-alanyl}amino-6-cyclohexyl-4-hydroxy-2,N-dimethylhexanamide

21(a) (3R, 5S)-5-[(1S)-1-{N-[2(R)-Benzyl-3-(morpholinocarbonyl)propionyl]-3-(4-thiazolyl)-L-alanyl}amino-2-cyclohexylethyl]-3-methyldihydrofuran-2(3H)-one A mixture of 1.7 g (3.64 mmole) of (3R, 5S)-5-{(1S)-1-[N-(t-butoxycarbonyl)-3-(4-thiazolyl)-L-alanyl]amino-2-cyclohexylethyl}-3-methyldihydrofuran-2(3H)-one (prepared as described in Preparation 25) and 20 ml of a 4N solution of hydrogen chloride in dioxane was stirred at room temperature for 60 minutes. At the end of this time, the solvent was removed by distillation under reduced pressure. Diethyl ether was added to the residue, and the resulting mixture was concentrated by evaporation under reduced pressure. This operation was repeated three times, in total. After the final residue had been dried under reduced pressure for 8 hours, the dried materials were suspended in 30 ml of anhydrous tetrahydrofuran. 1.11 g (4.0 mmole) of 2(R)-benzyl-3-(morpholinocarbonyl)propionic acid were then added to the suspension, after which 0.71 ml (4.37 mmole) of 95% diethyl cyanophosphonate and 2.0 ml (14.56 mmole) of triethylamine were added to the resulting mixture, whilst ice-cooling and under an atmosphere of nitrogen. The mixture was then stirred at room temperature for 15 hours, after which the solvent was removed by distillation under reduced pressure. The resulting residue was purified by medium pressure column chromatography through silica gel (using ethyl acetate as the eluent), to afford 1.43 g of the title compound as a colourless amorphous product.

Elemental analysis: Calculated for $C_{34}H_{46}N_4O_5S.\frac{1}{2}H_2O$: C, 63.04%; H, 7.31%; N, 8.65%; S, 4.95%. Found: C, 63.28%; H, 7.38%; N, 8.54%; S, 4.70%.

21(b) (2R, 4S, 5S)-5-{N-[2(R)-Benzyl-3-(morpholinocarbonyl)propionyl]-3-(4-thiazolyl)-L-alanyl}amino-6-cyclohexyl-4-hydroxy-2,N-dimethylhexanamide A solution of 200 mg (0.313 mmole) of (3R, 5S)-5-[(1S)-1-{N-[2(R)-benzyl-3-(morpholinocarbonyl)propionyl]-3-(4-thiazolyl)-L-alanyl}amino-2-cyclohexylethyl]-3-methyldihydrofuran-2(3H)-one [prepared as described in Preparation 21(a) above] in 2 ml of methanol was added, whilst ice-cooling, to 2.5 ml of a 40% by volume methanolic solution of methylamine, and the mixture was allowed to stand at room temperature for 1 hour. At the end of this time, any excess of the methylamine and the methanol were removed by distillation under reduced pressure. The resulting residue was dissolved in 4 ml of ethyl acetate, and the solution was allowed to stand overnight at room temperature to deposit crystals. These were collected by filtration to afford 150 mg of the title compound as white crystals, melting at 130°–132° C.

Elemental analysis: Calculated for $C_{35}H_{51}N_5O_6S$: C, 62.75%; H, 7.67%; N, 10.45%; S, 4.79%. Found: C, 62.74%; H, 7.78%; N, 10.25%; S, 4.79%.

PREPARATION 1

(3S, 5S)-5-[(1S)-1-(t-Butoxycarbonyl)amino-2-cyclohexylethyl]-3-isopropyldihydrofuran-2(3H)-one 1(a) (3S, 5S)-5-[(1S)-1-(t-Butoxycarbonyl)amino-2-cyclohexylethyl]-3-(1-hydroxy-1-methylethyl)dihydrofuran-2(3H)-one 15.81 ml (25.3 mmole) of butyllithium (as a 1.6M solution in hexane) were added, at −78° C. and under an atmosphere of nitrogen, to a solution of 3.55 ml (25.3 mmole) of diisopropylamine in 30 ml of anhydrous tetrahydrofuran, and the mixture was stirred for 30 minutes. A solution of 3.58 g (11.5 mmole) of (5S)-5-[(1S)-1-(t-butoxycarbonyl)amino-2-cyclohexylethyl]dihydrofuran-2(3H)-one in 10 ml of anhydrous tetrahydrofuran was then added to the mixture, and the mixture was stirred at −78° C. for 1 hour. 1.86 ml (25.3 mmole) of acetone purified by distillation was added to the mixture, after which the mixture was stirred for a further 2 hours. At the end of this time, the reaction mixture was mixed with a saturated aqueous solution of ammonium chloride and extracted with ethyl acetate. The organic layer was washed, in turn, with a 10% w/v aqueous solution of citric acid, with water and with a saturated aqueous solution of sodium chloride, after which it was dried over anhydrous magnesium sulfate. The solvent was then removed by distillation under reduced pressure and the residue was purified by medium pressure column chromatography through silica gel (using a 1:1 by volume mixture of hexane and diethyl ether as the eluent). The title compound, obtained from the less polar fractions, was isolated as white crystals, melting at 123°–125° C., and the amount obtained was 3.65 g (yield 86%).

$[\alpha]_D^{20} = -20.6°$ (c=1, methanol).

Elemental analysis: Calculated for $C_{20}H_{35}NO_5$: C, 65.01%; H, 9.55%; N, 3.79%. Found: C, 65.01%; H, 9.62%; N, 3.91%.

Mass spectrum (m/e): 369 (M+), 226, 170, 126.

The diastereomer of the title compound having the 3R-configuration was recovered from the more polar fractions as white crystals, melting at 141°–143° C., and the amount obtained was 290 mg (yield 7%).

$[\alpha]_D^{20} = -30.4°$ (c=1, methanol).

Elemental analysis: Calculated for $C_{20}H_{35}NO_5$: C, 65.01%; H, 9.55%; N, 3.79%. Found: C, 64.99%; H, 9.66%; N, 3.91%.

Mass spectrum (m/e): 369 (M+), 226, 170, 126.

1(b) (3S, 5S)-5-[(1S)-1-(t-Butoxycarbonyl)amino-2-cyclohexylethyl]-3-isopropyldihydrofuran-2(3H)-one 1.62 ml (11.6 mmole) of triethylamine and 5 mg of 4-(N,N-dimethylamino)pyridine were added to a solution of 2.15 g (5.82 mole) of (3S, 5S)-5-[(1S)-1-(t-butoxycarbonyl)amino-2-cyclohexylethyl]-3-(1-hydroxy-1-methylethyl)dihydrofuran-2(3H)-one in 20 ml of anhydrous tetrahydrofuran. 1.07 ml (11.6 mmole) of methyl oxalyl chloride were then added dropwise to the mixture, whilst ice-cooling and under an atmosphere of nitrogen, after which the mixture was stirred for 2 hours. At the end of this time, the solvent was removed by distillation under reduced pressure. The resulting residue was mixed with ethyl acetate and washed with a saturated aqueous solution of sodium chloride, after which it was dried over anhydrous magnesium sulfate. After the solvent had been removed by distillation under reduced pressure, the residue was purified by medium pressure column chromatography through silica gel (using a 1:4 by volume mixture of ethyl acetate and hexane as the eluent) to afford 2.61 g of an oxalyl ester compound (yield 99%).

2.37 g (5.20 mmole) of this oxalyl ester were dissolved in 30 ml of toluene, and 2.61 g (8.97 mmole) of tributyltin hydride and 427 mg (2.60 mmole) of azobis(isobutyronitrile) were added to the resulting solution. The mixture was then heated under reflux for 2 hours under an atmosphere of nitrogen, after which the solvent was removed by distillation under reduced pressure. The resulting residue was purified by medium pressure column chromatography through silica gel (using a 6:1 by volume mixture of hexane and ethyl acetate as the eluent), followed by recrystallization from hexane, to afford 1.39 g (yield 76%) of the title compound as white crystals, melting at 114°–116° C.

$[\alpha]_D^{20} = -25.0°$ (c=1, methanol).

Elemental analysis: Calculated for $C_{20}H_{35}NO_4$: C, 67.95%; H, 9.98%; N, 3.96%. Found: C, 67.63%; H, 9.92%; N, 4.07%.

Mass spectrum (m/e): 353 (M+), 170, 126.

PREPARATION 2

(3R, 5S)-5-[(1S)-1-(t-Butoxycarbonyl)amino-2-cyclohexylethyl]-3-methyldihydrofuran-2(3H)-one 2.83 ml (7.07 mmole) of butyllithium (as a 2.5M solution in hexane) were added, at −78° C. and under an atmosphere of nitrogen, to a solution of 0.99 ml (7.07 mmole) of diisopropylamine in 20 ml of anhydrous tetrahydrofuran. The resulting mixture was then stirred at the same temperature for 30 minutes, after which a solution of 1.0 g (3.2 mmole) of (5S)-5-[(1S)-1-(t-butoxycarbonyl)amino-2-cyclohexylethyl]dihydrofuran-2(3H)-one in 10 ml of anhydrous tetrahydrofuran was added to it. The mixture was then stirred at −78° C. for 30 minutes, after which 0.44 ml (7.07 mmole) of methyl iodide was added dropwise. The mixture was then allowed to stand at the same temperature for 1.5 hour, after which it was mixed with a saturated aqueous solution of ammonium chloride and then extracted with ethyl acetate. The organic layer was dried over anhydrous magnesium sulfate and then concentrated by distillation under reduced pressure. The resulting residue was purified by column chromatography through silica gel (using a 8:1 by volume mixture of hexane and ethyl acetate as the eluent) to afford a colorless oil. This oil was triturated with hexane to crystallize the product, and then the solvent was removed by distillation, to afford 0.69 g of the title compound as white crystals, melting at 80°–82° C.

Elemental analysis: Calculated for $C_{18}H_{31}NO_4$: C, 66.43%; H, 9.60%; N, 4.30%. Found: C, 66.24%; H, 9.67%; N, 4.38%.

PREPARATION 3

(2S, 4S, 5S)-5-(t-Butoxycarbonyl)amino-6-cyclohexyl-4-hydroxy-2-isopropyl-N-methylhexanamide Gaseous methylamine was introduced into a solution of 1.33 g (3.76 mmole) of (3S, 5S)-5-[(1S)-1-(t-butoxycarbonyl)amino-2-cyclohexylethyl]-3-isopropyldihydrofuran-2(3H)-one (prepared as described in Preparation 1) in 10 ml of methanol to ensure saturation, whilst ice-cooling. The reaction vessel was then stoppered tightly and allowed to stand overnight. At the end of this time, the solvent was removed by distillation under reduced pressure and the residue was recrystallized from hexane to afford 1.32 g (yield 91%) of the title compound as white crystals, melting at 154°–157° C.

$[\alpha]_D^{20} = -42.0°$ (c=0.75, methanol).

Elemental analysis: Calculated for $C_{21}H_{40}N_2O_4$: C, 65.59%; H, 10.48%; N, 7.28%. Found: C, 65.88%; H, 10.28%; N, 7.24%.

Infrared Absorption Spectrum (KBr) $\nu_{max}cm^{-1}$: 1666, 1629 $cm^{-1}$.

Mass spectrum (m/e): 385 (M++1), 158.

PREPARATION 4

(2S, 4S, 5S)-5-(t-Butoxycarbonyl)amino-6-cyclohexyl-4-hydroxy-2-isopropyl-N-butylhexanamide A mixture of 890 mg (2.52 mmole) of (3S, 5S)-5-[(1S)-1-(t-butoxycarbonyl)amino-2-cyclohexylethyl]-3-isopropyldihydrofuran-2(3H)-one (prepared as described in Preparation 1) and 2.5 ml (25.3 mmole) of butylamine was heated at 100° C. for 4 hours. At the end of this time, an excess of the butylamine was removed by distillation under reduced pressure, and the resulting residue was purified by medium pressure column chromatography through silica gel (using a 20:1 by volume mixture of methylene chloride and methanol as the eluent), followed by recrystallization from diisopropyl ether, to afford 1.05 g (yield 98%) of the title compound as white crystals, melting at 115°–118° C. $[\alpha]_D^{20} = -34.9°$ (c=1, methanol).

Elemental analysis: Calculated for $C_{24}H_{46}N_2O_4$: C, 67.57%; H, 10.87%; N, 6.57%. Found: C, 67.22%; H, 10.88%; N, 6.73%.

Infrared Absorption Spectrum (KBr) $\nu_{max}$ $cm^{-1}$: 1678, 1620 $cm^{-1}$.

Mass spectrum (m/e): 427 (M++1), 200.

PREPARATION 5

(2R, 4S, 5S)-5-(t-Butoxycarbonyl)amino-6-cyclohexyl-4-hydroxy-2,N-dimethylhexanamide Gaseous methylamine was introduced into a solution of 0.2 g (0.615 mole) of (3R, 5S)-5-[(1S)-1-(t-butoxycarbonyl)amino-2-cyclohexylethyl]-3-methyldihydrofuran-2(3H)-one (prepared as described in Preparation 2) in 6 ml of methanol for 3 minutes, after which the mixture was allowed to stand for 3 hours. The reaction mixture was then concentrated by distillation under reduced pressure, and the resulting residue was triturated with hexane to afford 0.23 g of the title compound as white crystals, melting at 144°–145° C.

Elemental analysis: Calculated for $C_{19}H_{36}N_2O_4$: C, 63.21%; H, 10.19%; N, 7.76%. Found: C, 63.28%; H, 10.36%; N, 7.72%.

PREPARATION 6

(2R, 4S, 5S)-5(t-Butoxycarbonyl)amino-N-butyl-6-cyclohexyl-4-hydroxy-2-methylhexanamide A mixture of 0.4 g (1.23 mmole) of (3R, 5S)-5-[(1S)-1-(t-butoxycarbonyl)amino-2-cyclohexylethyl]-3-methyldihydrofuran-2(3H)-one (prepared as described in Preparation 2) and 6 ml of butylamine was heated under reflux for 3.0 hours, whilst stirring. At the end of this time, the reaction mixture was concentrated by distillation under reduced pressure, after which the residue was purified by column chromatography through silica gel (using ethyl acetate as the eluent) to afford 0.48 g of the title compound as a white powder.

PREPARATION 7

(2R, 4S, 5S)-5-(t-Butoxycarbonyl)amino-6-cyclohexyl-N-hexyl-4-hydroxy-2-methylhexanamide A mixture of 450 mg (1.38 mmole) of (3R, 5S)-5-[(1S)-1-(t-butoxycarbonyl)amino-2-cyclohexylethyl]-3-methyldihydrofuran-2(3H)-one (prepared as described in Preparation 2) and 10 ml of hexylamine was heated under reflux for 2.2 hours, whilst stirring. At the end of this time, the reaction mixture was concentrated by distillation under reduced pressure, after which the residue was purified by column chromatography through silica gel (using a 1:2 by volume mixture of cyclohexane and ethyl acetate as the eluent) to afford 443 mg of the title compound as white crystals.

PREPARATION 8

(4S)-(−)-4-Benzyl-N-(3-phenylpropionyl)-2-oxazolidinone 48.1 ml (77 mmole) of butyllithium (as a 1.6M solution in hexane) were added dropwise, at −78° C. and under an atmosphere of nitrogen, to a solution of 12.41 g (70 mmole) of (4S)-(−)-4-benzyl-2-oxazolidinone in 200 ml of anhydrous tetrahydrofuran, and the mixture was stirred for 30 minutes. At the end of this time, a solution of 13.0 g (77 mmole) of 3-phenylpropionyl chloride in 100 ml of anhydrous tetrahydrofuran was slowly added dropwise to the mixture, and the mixture was stirred for 1 hour. The mixture was then mixed with a saturated aqueous solution of sodium chloride and extracted with ethyl acetate. The organic layer was dried over anhydrous magnesium sulfate and concentrated by distillation under reduced-pressure. The residue was purified by column chromatography through silica gel (using a 1:4 by volume mixture of ethyl acetate and hexane as the eluent) to afford 16.8 g (yield 78%) of the title compound as white crystals, melting at 92°–95° C.

Elemental analysis: Calculated for $C_{19}H_{19}NO_3$: C, 73.77%; H, 6.19%; N, 4.53%. Found: C, 73.57%; H, 6.28%; N, 4.41%.

Mass spectrum (m/e): 309 (M+).

PREPARATION 9

(4S)-(−)-4-Benzyl-N-[2(R)-benzyl-3-(benzyloxycarbonyl)-propionyl]-2-oxazolidinone 2.91 ml (20.8 mmole) of diisopropylamine and 13.40 ml (21.4 mmole) of butyllithium (as a 1.6M solution in hexane) were added, at −78° C. and under an atmosphere of nitrogen, to 50 ml of anhydrous tetrahydrofuran, and the mixture was stirred for 30 minutes. A solution of 5.35 g (17.3 mmole) of (4S)-(−)-4-benzyl-N-(3-phenylpropionyl)-2-oxazolidinone in 20 ml of anhydrous tetrahydrofuran was added to the resulting mixture, and then the mixture was stirred at the same temperature for 1 hour. At the end of this time, a solution of 5.74 ml (36.2 mmole) of benzyl bromoacetate in 10 ml of anhydrous tetrahydrofuran was added dropwise to the mixture, and then the mixture was stirred for 3 hours. At the end of this time, a saturated aqueous solution of sodium chloride was added to the mixture, which was then extracted with ethyl acetate. The organic layer was dried over anhydrous magnesium sulfate and concentrated by distillation under reduced pressure. The residue was purified by medium pressure column chromatography through silica gel (using a 1:5 by volume mixture of ethyl acetate and hexane as the eluent) to afford 5.47 g (yield 69%) of the title compound as a colorless oil.

Mass spectrum (m/e): 457 (M+).

PREPARATION 10

(4S)-(−)-4-Benzyl-N-[2(R)-benzyl-3-morpholinocarbonyl)propionyl]-2-oxazolidinone A solution of 5.10 g (11.1 mmole) of (4S)-(−)-4-benzyl-N-[2(R)-benzyl-3-(benzyloxycarbonyl)-propionyl]-2-oxazolidinone (prepared as described in Preparation 9) in 100 ml of ethanol was stirred at room temperature for 3 hours under an atmosphere of hydrogen and in the presence of 500 mg of 10% w/w palladium-on-charcoal. At the end of this time, the catalyst was removed by filtration and the filtrate was concentrated by distillation under reduced pressure. The residue was dissolved in 50 ml of anhydrous tetrahydrofuran. 1.16 ml (13.3 mmole) of morpholine, 2.02 ml (13.3 mmole) of 95% diethyl cyanophosphonate and 1.86 ml (13.3 mmole) of triethylamine were then added, in that order, to the resulting solution, whilst ice-cooling and under an atmosphere of nitrogen, and the mixture was stirred for 2 hours. At the end of this time, the solvent was removed by distillation under reduced pressure, and the residue was purified by medium pressure column chromatography through silica gel (using a 1:1 by volume mixture of ethyl acetate and hexane as the eluent) to afford 3.90 g (yield 80%) of the title compound as white crystals, melting at 56°–59° C.

Elemental analysis: Calculated for $C_{25}H_{28}N_2O_5$: C, 68.79%; H, 6.47%; N, 6.42%. Found: C, 68.59%; H, 6.75%; N, 6.50%.

PREPARATION 11

2(R)-Benzyl-3-(morpholinocarbonyl)propionic acid 711 mg (16.9 mmole) of lithium hydroxide monohydrate were added, whilst ice-cooling, to a solution of 3.70 g (8.5 mmole) of (4S)-(−)-4-benzyl-N-[2(R)-benzyl-3-(morpholinocarbonyl)propionyl]-2-oxazolidinone (prepared as described in Preparation 10) in a mixture of 80 ml of tetrahydrofuran and 30 ml of water, and the mixture was then stirred at the same temperature for 3 hours. At the end of this time, the tetrahydrofuran was stripped from the reaction mixture by distillation under reduced pressure, and the residue was mixed with a 10% w/v aqueous solution of sodium hydroxide and then extracted with methylene chloride. The aqueous layer was adjusted to a pH value of 1 by the addition of concentrated hydrochloric acid, whilst ice-cooling, and was again extracted with methylene chloride. The latter methylene chloride extracts were combined, dried over anhydrous magnesium sulfate and concentrated by distillation under reduced pressure to afford 1.75 g (yield 75%) of the title compound as a white oily substance.

Mass spectrum (m/e): 277 (M+).

PREPARATION 12

4(S)-Isopropyl-3-(3-phenylpropionyl)-2-oxazolidinone 68.3 ml (0.11 mol) of butyllithium (as a 1.6M solution in hexane) were added dropwise, at −78° C. and under an atmosphere of nitrogen, to a solution of 11.75 g (91.0 mmole) of 4(S)-isopropyl-2-oxazolidinone in 200 ml of anhydrous tetrahydrofuran; the mixture was then stirred for 30 minutes, after which a solution of 18.41 g (0.11 mole) of phenylpropionyl chloride in 100 ml of anhydrous tetrahydrofuran was added to it over a period of 10 minutes. The mixture was then stirred for 1 hour, after which it was mixed with a saturated aqueous solution of ammonium chloride and extracted with ethyl acetate. The organic layer was dried over anhydrous magnesium sulfate and the solvent was then removed by distillation under reduced pressure. The residue was purified by medium pressure column chromatography through silica gel (using a 1:3 by volume mixture of ethyl acetate and hexane as the eluent), followed by recrystallization from diisopropyl ether, to afford 20.12 g (yield 85%) of the title compound as white crystals, melting at 62°–63° C.

$[\alpha]_D^{20} = +71.4°$ (c=1, chloroform).

Elemental analysis: Calculated for $C_{15}H_{19}NO_3$: C, 68.94%; H, 7.33%; N, 5.36%. Found: C, 68.89%; H, 7.12%; N, 5.43%.

Mass spectrum (m/e): 261 (M+), 130, 104, 91.

PREPARATION 13

3-[2(R)-Benzyl-3-(benzyloxycarbonyl)propionyl]-4(S)-isopropyl-2-oxazolidinone 22.50 ml (36.0 mmole) of butyllithium (as a 1.6M solution in hexane) were added dropwise, at −78° C. and under an atmosphere of nitrogen, to a solution of 5.05 ml (36.0 mmole) of diisopropylamine in 100 ml of anhydrous tetrahydrofuran, and the mixture was stirred for 30 minutes. At the end of this time, a solution of 7.84 g (30.0 mmole) of 4(S)-isopropyl-3-(3-phenyl-1-oxopropyl)-2-oxazolidinone (prepared as described in Preparation 12) in 50 ml of anhydrous tetrahydrofuran was added dropwise to the mixture. The mixture was then stirred for 1 hour, after which 14.26 ml (90.0 mmole) of benzyl bromoacetate were added to it. The mixture was stirred for 6 hours while the temperature of the reaction mixture was permitted to revert to room temperature. At the end of this time, the reaction mixture was mixed with a saturated aqueous solution of ammonium chloride and extracted with ethyl acetate. The organic layer was dried over anhydrous magnesium sulfate and the solvent was stripped from it by distillation under reduced pressure. The residue was purified by medium pressure column chromatography through silica gel (using a 1:3 by volume mixture of ethyl acetate and hexane as the eluent), followed by recrystallization from diisopropyl ether, to afford 9.05 g (yield 74%) of the title compound as white crystals, melting at 118°–120° C.

$[\alpha]_D^{20} = +86.6°$ (c=1, chloroform).

Elemental analysis: Calculated for $C_{24}H_{27}NO_5$: C, 70.40%; H, 6.65%; N, 3.42%. Found: C, 70.78%; H, 6.71%; N, 3.54%.

Mass spectrum (m/e): 409 (M+), 318, 130, 91.

PREPARATION 14

3-[2(R)-Benzyl-3-(N-benzyl-N-methylaminocarbonyl)-propionyl]-4(S)-isopropyl-2-oxazolidinone A solution of 1.03 g (2.52 mmole) of 3-[2(R)-benzyl-3-(benzyloxycarbonyl)propionyl]-4(S)-isopropyl-2-oxazolidinone (prepared as described in Preparation 13) in 20 ml of ethanol was stirred at room temperature for 4 hours under an atmosphere of hydrogen and in the presence of 100 mg of 10% w/w palladium-on-charcoal. The catalyst was then removed by filtration, and the filtrate was concentrated by distillation under reduced pressure. The residue was dissolved in 50 ml of anhydrous tetrahydrofuran, and 0.39 ml (3.02 mmole) of N-benzyl-N-methylamine, 0.46 ml of 95% diethyl cyanophosphonate and 0.42 ml of triethylamine were added, in that order, to the solution, whilst ice-cooling and under an atmosphere of nitrogen, after which the mixture was stirred for 6 hours. At the end of this time, the solvent was removed by distillation under reduced pressure, and the residue was purified by medium pressure column chromatography through silica gel using a 1:1 by volume mixture of ethyl acetate and hexane as the eluent), followed by recrystallization from diisopropyl ether, to afford 1.04 g (yield 98%) of the title compound as white crystals, melting at 60°–62° C.

$[\alpha]_D^{20} = +107.1°$ (c=1, chloroform).

Elemental analysis: Calculated for $C_{25}H_{30}N_2O_4$: C, 71.07%; H, 7.16%; N, 6.63%. Found: C, 70.59%; H, 7.14%; N, 6.51%.

PREPARATION 15

2(R)-Benzyl-3-(N-benzyl-N-methylaminocarbonyl)propionic acid 80 mg (1.89 mmole) of lithium hydroxide were added to a solution of 400 mg (0.95 mmole) of 3-[2(R)-benzyl-4-(N-benzyl-N-methylamino)-4-oxobutyryl]-4(R)-isopropyl-2-oxazolidinone (prepared as described in Preparation 14) in a mixture of 10 ml of tetrahydrofuran and 4 ml of water, and the mixture was stirred at room temperature for 5 hours. At the end of this time, the solvent was removed by distillation under reduced pressure, and the resulting residue was mixed with methylene chloride. The mixture was then extracted with a 10% w/v aqueous solution of sodium hydroxide. The aqueous layer was adjusted to a pH value of 2.0 by the addition of citric acid and was then extracted with methylene chloride. The methylene chloride extracts were combined, dried over anhydrous magnesium sulfate and concentrated by distillation under reduced pressure, to afford a colorless oil. This oil was triturated with hexane and the powder which deposited was collected by filtration and then recrystallized from diisopropyl ether, to afford 84 mg of the title compound as needles, melting at 119°–121° C.

Elemental analysis: Calculated for $C_{19}H_{21}NO_3$: C, 73.29%; H, 6.80%; N, 4.50%. Found: C, 72.74%; H, 7.10%; N, 4.29%.

PREPARATION 16

2(R)-(4-Methoxybenzyl)-3-(morpholinocarbonyl)propionic acid

A procedure similar to those described in Preparations 12–14 was repeated, but using 3-(4-methoxyphenyl)propionic acid as one of the starting materials and morpholine as the amine, to afford benzyl 2(R)-(4-methoxybenzyl)-3-(morpholinocarbonyl)propionate.

1.62 g (4.08 mmole) of this compound was dissolved in 50 ml of ethanol, and the solution was stirred at room temperature for 4 hours under an atmosphere of hydrogen and in the presence of 160 mg of 10% w/w palladium-on-charcoal. At the end of this time, the catalyst was removed by filtration and the filtrate was concentrated by distillation under reduced pressure, to afford 1.25 g of the title compound as a colorless oily substance.

Mass spectrum (m/e): 307 (M+).

PREPARATION 17

(2R, 4S, 5S)-5-(t-Butoxycarbonyl)amino-6-cyclohexyl-4-hydroxy-N-isobutyl-2-methylhexanamide A solution of 290 mg (0.93 mmole) of (3R, 5S)-5-[(1S)-1-(t-butoxycarbonyl)amino-2-cyclohexylethyl]-3-methyldihydrofuran-2(3H)-one (prepared as described in Preparation 2) in 3 ml of methanol was mixed with 3 ml of isobutylamine, and the mixture was allowed to stand overnight at room temperature. At the end of this time, the reaction mixture was concentrated by distillation under reduced pressure, and the residue was triturated with hexane to afford 340 mg of the title compound as colorless crystals, melting at 125°–126° C.

PREPARATION 18

(2R, 4S, 5S)-5-(t-Butoxycarbonyl)amino-6-cyclohexyl-4-hydroxy-2-methyl-N-propylhexanamide A solution of 293 mg (0.9 mmole) of (3R, 5S)-5-[(1S)-1-(t-butoxycarbonyl)amino-2-cyclohexylethyl]-3-methyldihydrofuran-2(3H)-one (prepared as described in Preparation 2) in 3 ml of methanol was mixed with 3 ml of propylamine, whilst ice-cooling, and the mixture was allowed to stand overnight at room temperature. At the end of this time, the reaction mixture was concentrated by distillation under reduced pressure, and the residue was triturated with hexane to afford 315 mg of the title compound as white crystals, melting at 115°–116° C.

PREPARATION 19

(2R, 4S, 5S)-5-(t-Butoxycarbonyl)amino-6-cyclohexyl-N-ethyl-4-hydroxy-2-methylhexanamide A solution of 325 mg (1.0 mmole) of (3R, 5S)-5-[(1S)-1-(t-butoxycarbonyl)amino-2-cyclohexylethyl]-3-methyldihydrofuran-2(3H)-one (prepared as described in Preparation 2) in 10 ml of a 23% by volume methanolic solution of ethylamine was allowed to stand at room temperature for 3 hours and 55 minutes, after which the solvent was removed by distillation under reduced pressure. The residue was then recrystallizated from diisopropyl ether, to afford 321 mg of the title compound as white crystals, melting at 126°–127° C.

PREPARATION 20

2(R)-Benzyl-3-(N-cyclohexyl-N-methylaminocarbonyl)propionic acid 100 mg (2.42 mmole) of lithium hydroxide were added to a solution of 500 mg (1.21 mmole) of 3-[2(R)-benzyl-4-(N-cyclohexyl-N-methylamino)-4-oxobutyryl]-4(S)-isopropyl-2-oxazolidinone (which had been prepared by a similar procedure to those described in Preparations 12–14) in a mixture of 10 ml of tetrahydrofuran and 4 ml of water, and the mixture was stirred at room temperature for 5 hours. At the end of this time, the solvent was removed by distillation under reduced pressure, and the resulting residue was mixed with an aqueous solution of sodium bicarbonate and extracted with methylene chloride. The aqueous layer was adjusted to a pH value of 2 by the addition of an aqueous solution of citric acid and was then extracted with methylene chloride. The latter methylene chloride extract was dried over anhydrous magnesium sulfate and concentrated by distillation under reduced pressure, to afford 130 mg of the title compound as an amorphous product.

Elemental analysis: Calculated for $C_{18}H_{25}NO_3$: C, 71.26%; H, 8.31%; N, 4.62%. Found: C, 71.41%; H, 8.20%; N, 4.78%.

PREPARATION 21

2(R)-(4-Methoxybenzyl)-3-(piperidinocarbonyl)propionic acid

A procedure similar to those described in Preparations 12–14 was repeated, but using 3-(4-methoxyphenyl)propionyl chloride as one of the starting materials and piperidine as the amine, to afford 3-[2(R)-(4-methoxybenzyl)-4-piperidino-4-oxobutyryl]-4(S)-isopropyl-2-oxazolidinone. 1.0 g (2.4 mmole) of this compound was dissolved in a mixture of 25 ml of tetrahydrofuran and 15 ml of water, and 200 mg (4.8 mmole) of lithium hydroxide were added to the resulting solution, after which the mixture was stirred overnight at room temperature. The solvent was then removed by distillation under reduced pressure, and ethyl acetate was added to the residue. The mixture was then extracted with an aqueous solution of sodium bicarbonate. The aqueous layer was acidified by adding 10% w/v aqueous hydrochloric acid and was then extracted with ethyl acetate. The extract was dried over anhydrous magnesium sulfate and concentrated by distillation under reduced pressure to afford 443 mg of the title compound as an oil.

$[\alpha]_D^{20} = +6.0°$ (c=1, methanol).

Elemental analysis: Calculated for $C_{17}H_{23}NO_4$: C, 66.86%; H, 7.59%; N, 4.59%. Found: C, 66.62%; H, 7.67%; N, 4.35%.

PREPARATION 22

3-(N-Benzyl-N-methylaminocarbonyl)-2(R)-(4-methoxybenzyl)propionic acid

A procedure similar to those described in Preparations 12–14 was repeated, but using 3-(4-methoxyphenyl)propionyl chloride as one of the starting materials and N-benzyl-N-methylamine as the amine, to afford 3-[4-(N-benzyl-N-methylamino)-2(R)-(4-methoxybenzyl)-4-oxobutyryl]-4(S)-isopropyl-2-oxazolidinone. 1.0 g (2.35 mmole) of this compound was dissolved in a mixture of 25 ml of tetrahydrofuran and 10 ml of water, and 200 mg (4.8 mmole) of lithium hydroxide were added to the resulting solution. The mixture was then stirred at room temperature for 23 hours. At the end of this time, the solvent was removed by distillation under reduced pressure, and the residue was diluted with ethyl acetate and extracted with an aqueous solution of sodium bicarbonate. The aqueous layer was adjusted to a pH value of 2 by the addition of an aqueous solution of citric acid and was then extracted with methylene chloride. The combined methylene chloride extracts were dried over anhydrous magnesium sulfate and concentrated by distillation under reduced pressure to afford 390 mg of the title compound as an oil.

Elemental analysis: Calculated for $C_{20}H_{23}NO_4$: C, 70.36%; H, 6.79%; N, 4.10%. Found: C, 70.52%; H, 6.48%; N, 4.25%.

PREPARATION 23

Benzyl 2(R)-(4-methoxybenzyl)-3-(N-methylpiperazinocarbonyl)propionate hydrochloride A procedure similar to those described in Preparations 12–14 was repeated, but using 3-(4-methoxyphenyl)propionyl chloride as one of the starting materials and N-methylpiperazine as the amine, to afford 3-[2(R)-(4-methoxybenzyl)-4-(N-methylpiperazino)-4-oxobutyryl]-4(S)-isopropyl-2-oxazolidinone. 1.0 g (2.3 mmole) of this compound was dissolved in 10 ml of tetrahydrofuran, and the resulting solution was added dropwise, whilst ice-cooling and under an atmosphere of nitrogen, to a solution of 0.48 ml (4.6 mmole) of benzyl alcohol in 35 ml of tetrahydrofuran containing 1.38 ml (3.45 mmole) of butyllithium (as a 2.5M solution in hexane). The mixture was then stirred for 1 hour under the same conditions. At the end of this time, the mixture was mixed with an aqueous solution of ammonium chloride and was then extracted with ethyl acetate. The extracts were dried over anhydrous magnesium sulfate and concentrated by evaporation under reduced pressure. The residue was purified by column chromatography through silica gel (using methylene chloride containing 5% v/v methanol as the eluent) to afford 0.58 g of an oil. The whole of this oil was dissolved in dioxane, and the resulting solution was adjusted to a pH value of 1 by the addition of a 4N solution of hydrogen chloride in dioxane followed by distilling off the solvent under reduced pressure. The residue was mixed with acetone and, after allowing it to stand, 0.6 g of the title compound was obtained as a colorless powder, melting at 188°–190° C.

Elemental analysis: Calculated for $C_{24}H_{30}N_2O_4 \cdot HCl \cdot \frac{1}{2}H_2O$: C, 63.22%; H, 7.07%; N, 6.14%; Cl, 7.78%. Found: C, 63.60%; H, 7.01%; N, 6.19%; Cl, 7.56%.

PREPARATION 24

2(R)-(4-Methoxybenzyl)-3-(N-methylpiperazinocarbonyl)-propionic acid hydrochloride A suspension of 0.55 g of benzyl 2(R)-(4-methoxybenzyl)-3-(N-methylpiperazinocarbonyl)propionate hydrochloride (prepared as described in Preparation 23) in 20 ml of ethanol was stirred at room temperature for 4 hours under an atmosphere of hydrogen and in the presence of 0.2 g of 10% w/w palladium-on-charcoal. After removing the catalyst by filtration, the filtrate was concentrated by distillation under reduced pressure. The residue was mixed with ethanol and, after the mixture had been allowed to stand, 0.25 g of the title compound was obtained as a colorless powder, melting at 117°–118° C. (with decomposition)

Elemental analysis: Calculated for $C_{17}H_{24}N_2O_4 \cdot HCl \cdot 2H_2O$: C, 52.34%; H, 7.38%; N, 7.08%; Cl, 8.96%. Found: C, 52.79%; H, 6.88%; N, 6.98%; Cl, 8.97%.

PREPARATION 25

(3R, 5S)-5-{(1S)-1-[N-(t-Butoxycarbonyl)-3-(4-thiazolyl)-L-alanyl]amino-2-cyclohexylethyl}-3-methyldihydrofuran-2(3H)-one A mixture of 513 mg (1.58 mmole) of (3R, 5S)-5-[(1S)-1-(t-butoxycarbonyl)amino-2-cyclohexylethyl]-3-methyldihydrofuran-2(3H)-one (prepared as described in Preparation 2) and 20 ml of a 4N solution of hydrogen chloride in dioxane was stirred at room temperature for 65 minutes. At the end of this time, the solvent was stripped from the mixture by distillation under reduced pressure, and diethyl ether was added to the residue. The resulting mixture was then concentrated by evaporation under reduced pressure. This operation was repeated three times, in total, after which the final residue was dried by evaporation under reduced pressure for 8 hours. At the end of this time, the dried materials were suspended in 30 ml of anhydrous tetrahydrofuran, and 460 mg (1.69 mmole) of N-(t-butoxycarbonyl)-3-(4-thiazolyl)-L-alanine were added to the suspension. 0.27 ml (1.69 mmole) of 95% diethyl cyanophosphonate and 0.88 ml (6.34 mmole) of triethylamine were then added to the mixture, whilst ice-cooling and under an atmosphere of nitrogen. The mixture was then stirred at room temperature for 6 hours, after which the solvent was removed by distillation under reduced pressure. The resulting residue was mixed with 50 ml of water to deposit gummy materials. These were collected by filtration and washed with water. They were then dissolved in methylene chloride. The resulting solution was dried over anhydrous magnesium sulfate, and the solvent was then removed by distillation under reduced pressure. The residue was recrystallized from diisopropyl ether to afford 532 mg of the title compound as white crystals, melting at 118°–120° C.

Elemental analysis: Calculated for $C_{24}H_{37}N_3O_5S$: C, 60.10%; H, 7.78%; N, 8.76%; S, 6.69%. Found: C, 60.17%; H, 7.77%; N, 8.69%; S, 6.86%.

PREPARATION 26

(2R, 4S, 5S)-5-[N-(t-Butoxycarbonyl)-3-(4-thiazolyl)-L-alanyl]amino-6-cyclohexyl-4-hydroxy-2,N-dimethylhexanamide A solution of 500 mg (1.04 mmole) of (3R, 5S)-5-{(1S)-1-[N-(t-butoxycarbonyl)-3-(4-thiazolyl)-L-alanyl]amino-2-cyclohexylethyl}-3-methyldihydrofuran-2(3H)-one (prepared as described in Preparation 25) in 2.5 ml of a 40% by volume methanolic solution of methylamine was allowed to stand at room temperature for 1 hour. At the end of this time, any excess of the methylamine and the methanol were removed by distillation under reduced pressure. The resulting residue was recrystallized from ethyl acetate to afford 405 mg of the title compound as white crystals, melting at 158°–160° C.

Elemental analysis: Calculated for $C_{25}H_{42}N_4O_5S$: C, 58.80%; H, 8.29%; N, 10.97%; S, 6.28%. Found: C, 58.68%; H, 8.12%; N, 10.93%; S, 6.04%.

We claim:

1. A compound of formula (I):

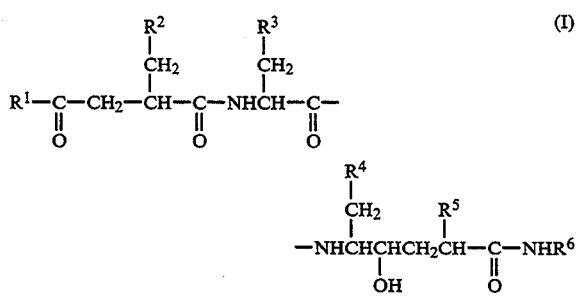

wherein $R^1$ is a 1-pyrrolidinyl, piperidino, morpholino, thiomorpholino, 1-piperazinyl, 4-methyl-1-piperazinyl or 4-phenyl-1-piperazinyl group or a group of formula —N($R^7$)($R^8$), wherein $R^7$ is a methyl group and $R^8$ is a benzyl, phenethyl, 4-methylbenzyl, 4-methoxybenzyl or 4-chlorobenzyl group;

$R^2$ is a phenyl or methoxyphenyl group, $R^3$ is a thiazolyl group;

$R^4$ is a cyclohexyl group;

$R^5$ is a $C_1$–$C_4$ alkyl group; and $R^6$ is a $C_1$–$C_6$ alkyl group.

2. The compound of claim 1, wherein the carbon atom indicated by an asterisk in the moiety of formula:

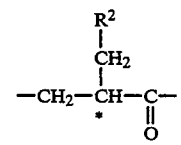

is in the R configuration.

3. A compound of formula (I):

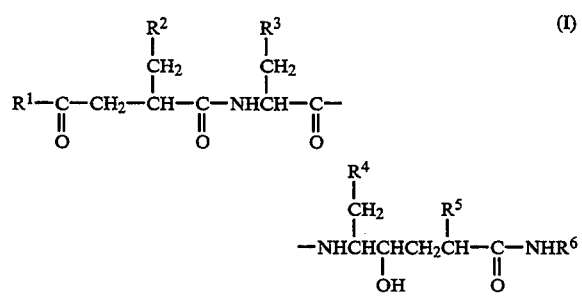

wherein $R^1$ represents a morpholine or N-benzyl-N-methylamino group;

$R^2$ represents a phenyl or methoxyphenyl group;

$R^3$ represents a thiazolyl group;

$R^4$ represents a cyclohexyl group;

$R^5$ represents a $C_1$–$C_4$ alkyl group;

$R^6$ represents a $C_1$–$C_6$ alkyl group;

or a pharmaceutically acceptable salt thereof.

4. The compound of claim 3, wherein the carbon atom indicated by an asterisk in the moiety of formula:

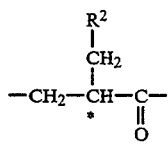

is in the R configuration.

5. The compound of claim 3, wherein the carbon atom indicated by an asterisk in the moiety of formula:

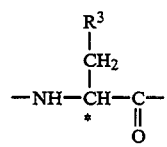

is in the S configuration.

6. The compound of claim 3, wherein the carbon atom indicated by an asterisk in the moiety of formula:

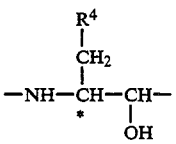

is in the S configuration.

7. The compound of claim 3, wherein the carbon atom indicated by an asterisk in the moiety of formula:

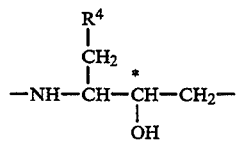

is in the S configuration.

8. The compound of claim 3, wherein the carbon atom indicated by a double asterisk in the moiety of formula:

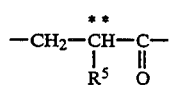

has the configuration:

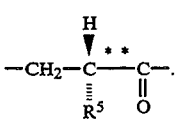

9. The compound of claim 3, wherein the carbon atoms indicated by a single asterisk in the moiety of formula:

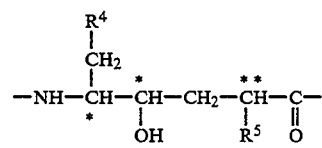

are all in the S configuration and the carbon atom indicated by the double asterisk has the configuration:

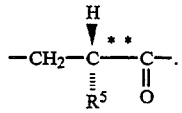

10. The compound of claim 3, wherein the carbon atom indicated by an asterisk in the moiety of formula:

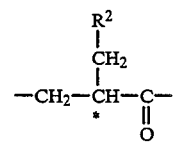

is in the R configuration and all of the carbon atoms indicated by single asterisks in the moiety of formula:

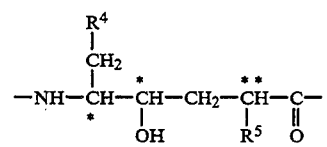

are in the S configuration and the carbon atom indicated by the double asterisk has the configuration:

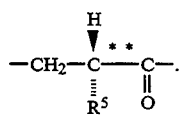

11. The compound of claim 3, wherein the carbon atom indicated by an asterisk in the moiety of formula:

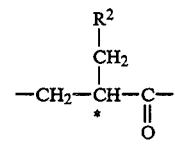

is in the R configuration and all of the carbon atoms indicated by single asterisks in the moiety of formula:

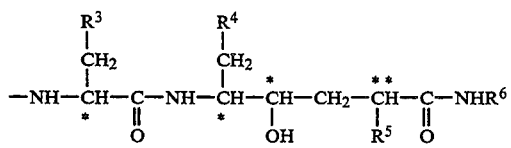

are in the S configuration and the carbon atom indicated by the double asterisk has the configuration:

$$-CH_2-C{=\!\!=\!\!=}C-.$$
$$\phantom{-CH_2-}{\overset{H}{\underset{R^5}{|}}}\phantom{==}{\overset{**}{\underset{O}{\|}}}$$

12. The compound of claim 1, wherein the carbon atom indicated by an asterisk in the moiety of formula:

$$-NH-\overset{*}{CH}-\overset{\overset{R^3}{|}}{\underset{\|}{C}}-$$
$$\phantom{-NH-CH-}\overset{CH_2}{\underset{O}{\|}}$$

is in the S configuration.

13. The compound of claim 1, wherein the carbon atom indicated by an asterisk in the moiety of formula:

$$-NH-\overset{*}{CH}-CH-$$
$$\phantom{-NH-}\overset{\overset{R^4}{|}}{\underset{OH}{|}}\phantom{-}\overset{CH_2}{|}$$

is in the S configuration.

14. The compound of claim 1, wherein the carbon atom indicated by an asterisk in the moiety of formula:

$$-NH-\overset{*}{CH}-CH-CH_2-$$
$$\phantom{-NH-}\overset{\overset{R^4}{|}}{\underset{OH}{|}}\overset{CH_2}{|}$$

is in the S configuration.

15. The compound of claim 3, wherein $R^6$ represents a methyl, ethyl, propyl, isopropyl, butyl, isobutyl or hexyl group.

16. The compound of claim 1, wherein the carbon atom indicated by a double asterisk in the moiety of formula:

$$-CH_2-\overset{**}{CH}-C-$$
$$\phantom{-CH_2-}\overset{R^5}{|}\ \overset{\|}{O}$$

has the configuration:

$$-CH_2-C{=\!\!=\!\!=}C-.$$
$$\phantom{-CH_2-}{\overset{H}{\underset{R^5}{|}}}\phantom{==}{\overset{**}{\underset{O}{\|}}}$$

17. The compound of claim 1, wherein $R^3$ represents a 4-thiazolyl group.

18. The compound of claim 1, wherein the carbon atom indicated by a single asterisk in the moiety of formula:

$$-NH-\overset{*}{CH}-\overset{*}{CH}-CH_2-\overset{**}{CH}-C-$$
$$\phantom{-NH-}\overset{\overset{R^4}{|}}{\underset{OH}{|}}\phantom{==}\overset{R^5}{|}\ \overset{\|}{O}$$

are all in the S configuration and the carbon atom indicated by the double asterisk has the configuration:

$$-CH_2-C{=\!\!=\!\!=}C-.$$
$$\phantom{-CH_2-}{\overset{H}{\underset{R^5}{|}}}\phantom{==}{\overset{**}{\underset{O}{\|}}}$$

19. The compound of claim 1, wherein the carbon atom indicated by an asterisk in the moiety of formula:

$$-CH_2-\overset{*}{CH}-C-$$
$$\phantom{-CH_2-}\overset{\overset{R^2}{|}}{\underset{O}{\|}}\overset{CH_2}{|}$$

is in the R configuration and all of the carbon atoms indicated by single asterisks in the moiety of formula:

$$-NH-\overset{*}{CH}-\overset{*}{CH}-CH_2-\overset{**}{CH}-C-$$
$$\phantom{-NH-}\overset{\overset{R^4}{|}}{\underset{OH}{|}}\phantom{==}\overset{R^5}{|}\ \overset{\|}{O}$$

are in the S configuration and the carbon atom indicated by the double asterisk has the configuration:

$$-CH_2-C{=\!\!=\!\!=}C-.$$
$$\phantom{-CH_2-}{\overset{H}{\underset{R^5}{|}}}\phantom{==}{\overset{**}{\underset{O}{\|}}}$$

20. The compound of claim 1, wherein $R^1$ represents a morpholino group.

21. The compound of claim 11, wherein the carbon atom indicated by an asterisk in the moiety of formula:

$$-CH_2-\overset{*}{CH}-C-$$
$$\phantom{-CH_2-}\overset{\overset{R^2}{|}}{\underset{O}{\|}}\overset{CH_2}{|}$$

is in the R configuration and all of the carbon atoms indicated by single asterisks in the moiety of formula:

$$-NH-\overset{*}{CH}-C-NH-\overset{*}{CH}-\overset{*}{CH}-CH_2-\overset{**}{CH}-C-NHR^6$$
$$\phantom{-NH-}\overset{\overset{R^3}{|}}{\underset{O}{\|}}\overset{CH_2}{|}\phantom{-NH-}\overset{\overset{R^4}{|}}{\underset{OH}{|}}\overset{CH_2}{|}\phantom{==}\overset{R^5}{|}\ \overset{\|}{O}$$

are in the S configuration and the carbon atom indicated by the double asterisk has the configuration:

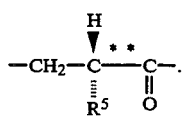

22. The compound of claim 1, wherein $R^6$ represents a methyl, ethyl, propyl, isopropyl, butyl, isobutyl or hexyl group.

23. The compound of claim 1, wherein $R^5$ represents a methyl, ethyl or isopropyl group.

24. The compound of claim 1, wherein $R^6$ represents a methyl, ethyl, propyl, butyl or isobutyl group.

25. The compound of claim 3, wherein:
   $R^1$ represents a morpholino or N-benzyl-N-methylamino group;
   $R^2$ represents a phenyl or methoxyphenyl group;
   $R^4$ represents a cyclohexyl group;
   $R^5$ represents a methyl, ethyl or isopropyl group; and
   $R^6$ represents a methyl, ethyl, propyl, butyl or isobutyl group.

26. The compound of claim 25, selected from the group consisting of 5-{N-[2-benzyl-3-(morpholinocarbonyl)propionyl]3-(4-thiazolyl)-L-alanyl}amino-6-cyclohexyl-4-hydroxy-2,N-dimethylhexanamide and pharmaceutically acceptable salts thereof.

27. The compound of claim 25, selected from the group consisting of (2R, 4S, 5S)-5-{N-[2(R)-benzyl-3-(morpholinocarbonyl)propionyl]-3-(4-thiazolyl)-L-alanyl}amino-6-cyclohexyl-4-hydroxy-2,N-dimethylhexanamide and pharmaceutically acceptable salts thereof.

28. The compound of claim 25, selected from the group consisting of 5-{N-[2-benzyl-3-(morpholinocarbonyl)propionyl]-3-(4-thiazolyl)-L-alanyl}amino-N-butyl-6-cyclohexyl-4-hydroxy-2-methylhexanamide and pharmaceutically acceptable salts thereof.

29. The compound of claim 25, selected from the group consisting of (2R, 4S, 5S)-5-{N-[2(R)-benzyl-3-(morpholinocaronyl)propionyl]-3-(4-thiazolyl)-L-alanyl}amino-L-butyl-6-cyclohexyl-4-hydroxy-2-methylhexanamide and pharmaceutically acceptable salts thereof.

30. The compound of claim 25, selected from the group consisting of 5-{N-[2(R)-benzyl-3-(morpholinocarbonyl)propionyl]-3-(4-thiazolyl)-L-alanyl}amino-6-cyclohexyl-N-hexyl-4-hydroxy-2-methylhexanamide and pharmaceutically acceptable salts thereof.

31. The compound of claim 25, selected from the group consisting of (2R, 4S, 5S)-5-{N-[2(R)-benzyl-3-(morpholinocarbonyl)propionyl]3-(4-thiazolyl )-L-alanyl}amino-6-cyclohexyl-N-hexyl-4-hydroxy-2-methylhexanamide and pharmaceutically acceptable salts thereof.

32. The compound of claim 25, selected from the group consisting of 5-{N-[2-benzyl-3-(morpholinocarbonyl)propionyl]-3-(4-thiazolyl)-L-alanyl}amino-6-cyclohexyl-4-hydroxy-2-isopropyl-N-methylhexanamide and pharmaceutically acceptable salts thereof.

33. The compound of claim 25, selected from the group consisting of (2S, 4S, 5S)-5-{N-[2(R)-benzyl-3-(morpholinocarbonyl)propionyl]-3-(4-thiazolyl)-L-alanyl}amino-6-cyclohexyl-4-hydroxy-2-isopropyl-N-methylhexanamide and pharmaceutically acceptable salts thereof.

34. The compound of claim 25, selected from the group consisting of 5-{N-[2-benzyl-3-(morpholinocarbonyl)propionyl]-3-(4-thiazolyl)-L-alanyl}amino-N-butyl-6-cyclohexyl-4-hydroxy-2-isopropylhexanamide and pharmaceutically acceptable salts thereof.

35. The compound of claim 25, selected from the group consisting of (2S, 4S, 5S)-5-{N-[2(R)-benzyl-3-(morpholinocarbonyl)propionyl]-3-(4-thiazolyl)-N-alanyl}amino-L-butyl-6-cyclohexyl-4-hydroxy-2-isopropylhexanamide and pharmaceutically acceptable salts thereof.

36. The compound of claim 25, selected from the group consisting of N-butyl-6-cyclohexyl-4-hydroxy-5-{N-[2-(4-methoxybenzyl)-3-(morpholinocarbonyl)propionyl]-3-(4-thiazolyl)-L-alanyl}amino-2-methylhexanamide and pharmaceutically acceptable salts thereof.

37. The compound of claim 25, selected from the group consisting of (2R, 4S, 5S)-N-butyl-6-cyclohexyl-4-hydroxy-5-{N-[2(R)-(4-methoxybenzyl)-3-(morpholinocarbonyl)propionyl]-3-(4-thiazolyl)-L-alanyl-}amino-2-methylhexanamide and pharmaceutically acceptable salts thereof.

38. The compound of claim 25, selected from the group consisting of 5-{N-[2-(4-methoxybenzyl)-3-(morpholinocarbonyl)propionyl]-3-(4-thiazolyl)-L-alanyl-}amino-6-cyclohexyl-4-hydroxy-2-isopropyl-N-methylhexanamide and pharmaceutically acceptable salts thereof.

39. The compound of claim 25, selected from the group consisting of (2S, 4S, 5S)-5-{N-[2(R)-(4-methoxybenzyl)-3-(morpholinocarbonyl)propionyl]-3-(4-thiazolyl)-L-alanyl}amino-6-cyclohexyl-4-hydroxy-2-isopropyl-N-methylhexanamide and pharmaceutically acceptable salts thereof.

40. The compound of claim 25, selected from the group consisting of N-butyl-6-cyclohexyl-4-hydroxy-2-isopropyl-5-{N-[2-(4-methoxybenzyl)-3-(morpholinocarbonyl)propionyl]-3-(4-thiazolyl)-L-alanyl)aminohexanamide and pharmaceutically acceptable salts thereof.

41. The compound of claim 25, selected from the group consisting of (2S, 4S, 5S)-N-butyl-6-cyclohexyl-4-hydroxy-2-isopropyl-5-{N-[2(R)-(4-methoxybenzyl)-3-(morpholinocarbonyl)propionyl]-3-(4-thiazolyl)-L-alanyl}aminohexanamide and pharmaceutically acceptable salts thereof.

42. A pharmaceutical composition for the treatment or prophylaxis of angiotensin-induced hypertension in an animal which comprises an effective amount of a compound of formula (I), as defined in claim 3, or of a pharmaceutically acceptable salt thereof in admixture with a pharmaceutically acceptable carrier or diluent.

43. A method for the treatment or prophylaxis of angiotensin-induced hypertension in an animal, by the administration thereto of an effective amount of a compound of formula (I), as defined in claim 3, or of a pharmaceutically acceptable salt thereof.

44. A pharmaceutical composition for the treatment or prophylaxis of angiotensin-induced hypertension in an animal which comprises an effective amount of a compound of formula (I), as defined in claim 1, or of a pharmaceutically acceptable salt thereof in admixture with a pharmaceutically acceptable carrier or diluent.

45. The composition of claim 44, wherein:
   $R^1$ represents a pyrrolidinyl, piperidinyl, morpholinyl, thiomorpholinyl, piperazinyl, 4-methylpiperazinyl or 4-phenylpiperazinyl group or a group of formula

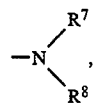

wherein $R^7$ represents a $C_1$–$C_4$ alkyl group and $R^8$ represents a $C_1$–$C_4$ alkyl group having a phenyl substituent, the phenyl substituent being unsubstituted or having at least one substituent selected from the group consisting of methyl groups, ethyl groups, methoxy groups and chlorine atoms;

$R^2$ represents a phenyl, tolyl, chlorophenyl, methoxyphenyl or naphthyl group; and $R^6$ represents a methyl, ethyl, propyl, isopropyl, butyl, isobutyl or hexyl group.

46. The composition of claim 44, wherein:

$R^1$ represents a pyrrolidinyl, piperidinyl, morpholinyl, thiomorpholinyl, piperazinyl, 4-methylpiperazinyl or 4-phenylpiperazinyl group or a group of formula

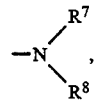

wherein $R^7$ represents a methyl or ethyl group and $R^8$ represents a benzyl, phenethyl, 4-methylbenzyl, 4-methoxybenzyl or 4-chlorobenzyl group;

$R^2$ represents a phenyl, tolyl, chlorophenyl, methoxyphenyl or naphthyl group; and $R^6$ represents a methyl, ethyl, propyl, isopropyl, butyl, isobutyl or hexyl group.

47. The composition of claim 44, wherein:

$R^1$ represents a morpholinyl or N-benzyl-N-methylamino group;

$R^2$ represents a phenyl or methoxyphenyl group;

$R^4$ represents a cyclohexyl group;

$R^5$ represents a methyl, ethyl or isopropyl group; and $R^6$ represents a methyl, ethyl, propyl, butyl or isobutyl group.

48. A method for the treatment or prophylaxis of angiotensin-induced hypertension in an animal by the administration thereto of an effective amount of a compound of formula (I), as defined in claim 1, or of a pharmaceutically acceptable salt thereof.

49. The method of claim 48, wherein:

$R^1$ represents a pyrrolidinyl, piperidinyl, morpholinyl, thiomorpholinyl, piperazinyl, 4-methylpiperazinyl or 4-phenylpiperazinyl group or a group of formula

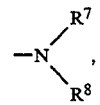

wherein $R^7$ represents a $C_1$–$C_4$ alkyl group and $R^8$ represents a $C_1$–$C_4$ alkyl group having a phenyl substituent, the phenyl substituent being unsubstituted or having at least one substituent selected from the group consisting of methyl groups, ethyl groups, methoxy groups and chlorine atoms;

$R^2$ represents a phenyl, tolyl, chlorophenyl, methoxyphenyl or naphthyl group; and $R^6$ represents a methyl, ethyl, propyl, isopropyl, butyl, isobutyl or hexyl group.

50. The method of claim 48, wherein:

$R^1$ represents a pyrrolidinyl, piperidinyl, morpholinyl, thiomorpholinyl, piperazinyl, 4-methylpiperazinyl or 4-phenylpiperazinyl group or a group of formula

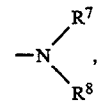

wherein $R^7$ represents a methyl or ethyl group and $R^8$ represents a benzyl, phenethyl, 4-methylbenzyl, 4-methoxybenzyl or 4-chlorobenzyl group;

$R^2$ represents a phenyl, tolyl, chlorophenyl, methoxyphenyl or naphthyl group; and $R^6$ represents a methyl, ethyl, propyl, isopropyl, butyl, isobutyl or hexyl group.

51. The method of claim 48, wherein:

$R^1$ represents a morpholinyl or N-benzyl-N-methylamino group;

$R^2$ represents a phenyl or methoxyphenyl group;

$R^4$ represents a cyclohexyl group;

$R^5$ represents a methyl, ethyl or isopropyl group; and $R^6$ represents a methyl, ethyl, propyl, butyl or isobutyl group.

52. The method of claim 48, wherein the animal is a mammal.

* * * * *